United States Patent
Hasty et al.

(10) Patent No.: US 11,612,580 B2
(45) Date of Patent: Mar. 28, 2023

(54) COMPOSITIONS FOR INHIBITING 3' REPAIR EXONUCLEASE 2 AND METHODS OF SCREENING FOR SUCH COMPOSITIONS

(71) Applicant: THE BOARD OF REGENTS OF THE UNIVERSITY OF TEXAS SYSTEM, Austin, TX (US)

(72) Inventors: Edward Paul Hasty, San Antonio, TX (US); Dmitri Nickolaevich Ivanov, San Antonio, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 16/756,705

(22) PCT Filed: Oct. 16, 2018

(86) PCT No.: PCT/US2018/055968
§ 371 (c)(1),
(2) Date: Apr. 16, 2020

(87) PCT Pub. No.: WO2019/079222
PCT Pub. Date: Apr. 25, 2019

(65) Prior Publication Data
US 2020/0253913 A1    Aug. 13, 2020

Related U.S. Application Data

(60) Provisional application No. 62/572,820, filed on Oct. 16, 2017.

(51) Int. Cl.
| | | |
|---|---|---|
| *A61K 31/24* | (2006.01) | |
| *C12Q 1/6806* | (2018.01) | |
| *C12N 15/113* | (2010.01) | |
| *A61K 31/136* | (2006.01) | |
| *A61K 31/192* | (2006.01) | |
| *A61K 31/352* | (2006.01) | |
| *A61K 31/405* | (2006.01) | |
| *A61K 31/53* | (2006.01) | |
| *A61K 31/655* | (2006.01) | |
| *A61K 49/00* | (2006.01) | |

(52) U.S. Cl.
CPC ............ *A61K 31/24* (2013.01); *A61K 31/136* (2013.01); *A61K 31/192* (2013.01); *A61K 31/352* (2013.01); *A61K 31/405* (2013.01); *A61K 31/53* (2013.01); *A61K 31/655* (2013.01); *A61K 49/0043* (2013.01); *C12N 15/113* (2013.01); *C12Q 1/6806* (2013.01); *C12Q 2600/136* (2013.01)

(58) Field of Classification Search
None
See application file for complete search history.

(56) References Cited

U.S. PATENT DOCUMENTS

| 6,831,106 B1 | 12/2004 | Bernardon et al. |
| 7,005,440 B1 | 2/2006 | Jayyosi et al. |
| 7,439,035 B1 * | 10/2008 | Parniak ................ C12Q 1/34 |
| | | 435/23 |
| 7,439,341 B2 * | 10/2008 | Laikhter ............... C07H 21/04 |
| | | 534/727 |
| 2017/0234884 A1 | 8/2017 | Baillie et al. |

OTHER PUBLICATIONS

National Center for Biotechnology Information. "PubChem Compound Summary for CID 1369, 8-Anilino-1-naphthalenesulfonic acid" PubChem, https://pubchem.ncbi.nlm.nih.gov/compound/8-Anilino-1-naphthalenesulfonic-acid. Accessed May 27, 2021. Created Mar. 25, 2005. (Year: 2005).*
Zhang et al., "Targeting prostate cancer cells with genetically engineered polypeptide-based micelles displaying gastrin-releasing peptide", 2016, International Journal of Pharmaceutics, 513(1-2), pp. 270-279. (doi.org/10.1016/j.ijpharm.2016.09.039) (Year: 2016).*
Johansson et al., "Intramolecular Dimers: A New Strategy to Fluorescence Quenching in Dual-Labeled Oligonucleotide Probes", 2002, Journal of the American Chemical Society, 124(24), pp. 6950-6956. (https://doi.org/10.1021/ja025678o) (Year: 2002).*
Perrino et al., "The Human TREX2 3'-> 5'-Exonuclease Structure Suggests a Mechanism for Efficient Nonprocessive DNA Catalysis", 2005, The Journal of Biological Chemistry, vol. 280, No. 15, pp. 15212-15218. (DOI 10.1074/jbc.M500108200) (Year: 2005).*
Wood et al., "Kinetic Analysis of Yersinia pestis DNA Adenine Methyltransferase Activity Using a Hemimethylated Molecular Break Light Oligonucleotide", 2007, PLoS ONE, issue 8, e801, pp. 1-7. (oi:10.1371/journal.pone.0000801). (Year: 2007).*
Lehtinen et al., "The TREX1 Double-stranded DNA Degradation Activity Is Defective in Dominant Mutations Associated with Autoimmune Disease", 2008, The Journal of Biological Chemistry, vol. 283, No. 46, pp. 31649-31656. (DOI 10.1074/jbc.M806155200) (Year: 2008).*
Hemphill et al., "Chapter Eight—Measuring TREX1 and TREX2 exonuclease activities", 2019, Methods in Enzymology, Editor(s): Jungsan Sohn, Academic Press, vol. 625, pp. 109-133. (https://www.sciencedirect.com/science/article/pii/S0076687919301636) (Year: 2019).*
Sheppard et al., "A universal fluorescence-based toolkit for real-time quantification of DNA and RNA nuclease activity", 2019, Scientific Reports, 9:8853, pp. 1-14. (https://doi.org/10.1038/s41598-019-45356-z) (Year: 2019).*
Glen Research Product of Black Hole Quencher Dyes, (https://www.glenresearch.com/products/labels-and-modifiers/label-phosphoramidites-and-supports/black-hole-quencher-dyes.html) Accessed Apr. 6, 2022. (Year: 2022).*

(Continued)

*Primary Examiner* — My-Chau T. Tran
(74) *Attorney, Agent, or Firm* — Womble Bond Dickinson (US) LLP

(57) ABSTRACT

Provided here are therapeutically effective pharmaceutical compositions containing one or more TREX2 inhibitors, and more specifically methods of administering TREX2 inhibitors to increase the effectiveness of a chemotherapeutic agent. Also provided here are methods of identifying agents that inhibit the exonuclease activity of TREX2.

9 Claims, 16 Drawing Sheets

(56) References Cited

OTHER PUBLICATIONS

National Center for Biotechnology Information. "PubChem Compound Summary for CID 59271212" PubChem, https://pubchem.ncbi.nlm.nih.gov/compound/59271212. Create Aug. 20, 2012. Accessed Apr. 6, 2022. (Year: 2012).*

International Search Report and Written Opinion for PCT/US2018/055968, Apr. 1, 2019.

PubChem CID 1406766, create date Jul. 11, 2005 [online]. [Retrieved Jan. 16, 2019]. Retrieved from the internet <URL: https://pubchem.ncbi.nlm.nih.gov/compound/1406766#section=Top> p. 3.

PubChem CID 5293426, create date Jun. 29, 2005 [online]. [Retrieved Jan. 16, 2019]. Retrieved from the internet <URL: https://pubchem.ncbi.nlm.nih.gov/compound/5293426#section=Top>.

Zhigang Zhou, et al., Multi-confirmation 3D QSAR study of benzenesulfonyl-pyrazol-ester compounds and their analogs as cathespin B inhibitors, National Institutes of Public Health, J Mol Graph Model. Sep. 2011; 30:135-147.

* cited by examiner

COMPOSITIONS FOR INHIBITING 3' REPAIR EXONUCLEASE 2 AND METHODS OF SCREENING FOR SUCH COMPOSITIONS

CROSS-REFERENCE TO RELATED APPLICATIONS

This application is a U.S. National Phase Under 35 U.S.C. § 371 of International Application No. PCT/US2018/055968, filed Oct. 16, 2018, titled "COMPOSITIONS FOR INHIBITING 3' REPAIR EXONUCLEASE 2 AND METHODS OF SCREENING FOR SUCH COMPOSITIONS," which is a PCT application claiming priority to and the benefit of U.S. Provisional Application No. 62/572,820, filed Oct. 16, 2017, titled "COMPOSITIONS FOR INHIBITING 3' REPAIR EXONUCLEASE 2 AND METHODS OF SCREENING FOR SUCH COMPOSITIONS," the entire contents of which are incorporated by reference herein.

GOVERNMENT SUPPORT

This invention was made with government support under Grant No. CA118032 awarded by the National Institutes of Health. The government has certain rights in the invention.

TECHNICAL FIELD

The present disclosure relates to methods of screening agents that alter the exonuclease activity of TREX2 and certain specific TREX2 inhibitors. Also disclosed are methods of evaluating TREX2 activity in both normal and cancer cells, and effects of TREX2 inhibitors in combination with other chemotherapeutic agents on cancer cells.

BACKGROUND

Double strand breaks (DSBs) in the chromosome occur spontaneously or as a result of normal cellular processes or environmental exposure to irradiation, chemical agents, or ultraviolet rays. If these DSBs are not repaired correctly, they can cause deletions, translocations, and fusions of the chromosomal DNA that result in genomic instability and cell death. DSBs activate the DNA damage response, which is dependent on the cell-cycle state. Several proteins are involved in the repair of DSBs by at least two different pathways. The first pathway is called recombinational repair and it utilizes a homologous template usually provided by the sister chromatid. The second pathway is called nonhomologous end joining (NHEJ) because it joins chromosomal ends without the use of a homologous template. Choice of the repair pathway can depend on the source and timing of the DSBs. TREX2 (Three prime Repair Exonuclease 2) is a 3'→5' exonuclease that removes 3' mismatches in DNA. TREX2 appears to increase genomic instability in both wild type and in DNA repair-mutant cells. However, its biological function is not well understood. Currently there are no successful drugs that enhance the effectiveness of chemotherapeutics/radiation therapy in killing cancer cells (but not normal cells) while inhibiting genomic instability in both cancer and normal cells. Standard laboratory practice for determining the activity of a nuclease involves incubating a sample containing oliognucleotides with the nuclease and then analyzing the resulting mixture with gel electrophoresis. An active nuclease will generate a ladder of multiple bands (caused by the nuclease degrading the oligonucleotide) whereas an inactive nuclease will result in a single band from the still intact oligonucleotide. The bands are typically visualized using a chelating agent like ethidium bromide. This process is moderately labor intensive, takes 1-2 hours, and involves unsafe reagents. There exists a need for safer and faster assays for detection of agents that alter activity of exonucleases.

SUMMARY

Disclosed herein are compounds and methods addressing these shortcomings of the art, and provide other additional or alternative advantages. The TREX2 inhibitors can enhance current cancer therapy while suppressing the risk of side effects that result from an increase in DNA damage and responses to that damage, which can cause fatigue, diarrhea, nausea and vomiting. TREX2 inhibitors should also reduce mutations, which can lead to long-term side effects, such as nervous system disorders and secondary cancers.

Embodiments include a therapeutically effective pharmaceutical composition containing 4-benzoyl-2-methyphenyl (2-nitrophenoxy) acetate, or pharmaceutically acceptable derivatives thereof. Embodiments also include methods of increasing effectiveness of a chemotherapeutic agent in a mammalian cancer cell. One such method includes the steps of administering to a mammalian cancer cell exposed to a chemotherapeutic agent, a therapeutically effective pharmaceutical composition containing 4-benzoyl-2-methyphenyl (2-nitrophenoxy) acetate, or pharmaceutically acceptable derivatives thereof.

Embodiments include a therapeutically effective pharmaceutical composition containing N-benzyl-2-([bis(furan-2-yl)-1,2,4-triazin-3-yl] sulfanyl) acetamide, or pharmaceutically acceptable derivatives thereof. Embodiments also include methods of increasing effectiveness of a chemotherapeutic agent in a mammalian cancer cell. One such method includes the steps of administering to a mammalian cancer cell exposed to the chemotherapeutic agent, a therapeutically effective pharmaceutical composition containing N-benzyl-2-([bis(furan-2-yl)-1,2,4-triazin-3-yl] sulfanyl) acetamide, or pharmaceutically acceptable derivatives thereof.

Embodiments include a therapeutically effective pharmaceutical composition containing 6-(benzylcarbamoyl)-1-methycyclohex-3-ene-1-carboxylic acid, or pharmaceutically acceptable derivatives thereof. Embodiments also include methods of increasing effectiveness of a chemotherapeutic agent in a mammalian cancer cell. One such method includes the steps of administering to a mammalian cancer cell exposed to the chemotherapeutic agent, a therapeutically effective pharmaceutical composition containing 6-(benzylcarbamoyl) -1-methycyclohex-3-ene-1-carboxylic acid, or pharmaceutically acceptable derivatives thereof.

Embodiments include a therapeutically effective pharmaceutical composition containing 8-(phenylamino)naphthalene-1-sulfonic acid, or pharmaceutically acceptable derivatives thereof. Embodiments also include methods of increasing effectiveness of a chemotherapeutic agent in a mammalian cancer cell. One such method includes the steps of administering to a mammalian cancer cell exposed to the chemotherapeutic agent, a therapeutically effective pharmaceutical composition containing 8-(phenylamino)naphthalene- 1-sulfonic acid, or pharmaceutically acceptable derivatives thereof.

Embodiments include a therapeutically effective pharmaceutical composition containing benzyl 6-(furan-2-yl)-3-methyl-4-oxo-4,5,6,7-tetrahydro-$^1$H-indole-2-carboxylate, or pharmaceutically acceptable derivatives thereof. Embodiments also include methods of increasing effectiveness of a chemotherapeutic agent in a mammalian cancer cell. One such method includes the steps of administering to a mammalian cancer cell exposed to the chemotherapeutic agent, a therapeutically effective pharmaceutical composition containing benzyl 6-(furan-2-yl)-3-methyl-4-oxo-4,5,6,7-tetrahydro-$^1$H-indole-2-carboxylate, or pharmaceutically acceptable derivatives thereof.

Embodiments also include methods of identifying an agent that inhibits the exonuclease activity of TREX2. One such method includes the steps of providing an oligonucleotide-based substrate with a reporter associated with 3' end of the oligonucleotide-based substrate and a complementary quencher associated with 5' end of the oligonucleotide-based substrate, followed by incubating the oligonucleotide-based substrate in the presence of TREX2 and a compound under reaction conditions for a sufficient period of time, and then determining the amount of reporter disassociated from the oligonucleotide-based substrate. An increase in the amount of reporter disassociated from the oligonucleotide-based substrate indicates that the compound is an agent that inhibits exonuclease activity of TREX2. The oligonucleotide-based substrate is a single stranded deoxyribonucleic acid. The oligonucleotide-based substrate can be a 20 nucleotide-long single stranded deoxyribonucleic acid. The reporter can be covalently attached to the base of the second to last nucleotide on the 3' end. The reporter can be located at 25 nucleotides or less from the complementary quencher. The reporter can be a fluorophore. In certain embodiments, the reporter is fluorescein. In certain embodiments, the complementary quencher is 4'-(4-Nitro-phenyldiazo)-2'-methoxy-5'-methoxy-azobenzene-4"-(N-2-oxy ethyl (4,4' dimethoxy trityl))-N-ethyl-2-cyanoethyl-(N,N-diisopropyl)-phosphoramidite (Black Hole® Quencher). In certain embodiments, the reporter can be tetramethylrhodamine (TAMRA) and the complementary quencher is Iowa Black® Red Quencher.

Numerous other aspects, features and benefits of the present disclosure may be made apparent from the following detailed description taken together with the drawings. The pharmaceutical compositions can include compounds described herein, other components, or ingredients depending on desired prevention and treatment goals. It should be further understood that both the foregoing general description and the following detailed description are exemplary and explanatory and are intended to provide further explanation of the embodiments as claimed.

BRIEF DESCRIPTION OF THE DRAWINGS

The present disclosure can be better understood by referring to the following figures. The components in the figures are not necessarily to scale. The emphasis is instead placed upon illustrating the principles of the disclosure. In the figures, reference numerals designate corresponding parts throughout the different views.

FIG. 8A is a graphical representation of the percentage of TG-resistant cells, following the exposure of the RAD51$^{K133A}$ expressing cells to Compounds 1, 6, and 10. FIG. 8B is a photographic image of the plates with puromycin resistant cells, treated with a vehicle or a TREX2 inhibitor. FIG. 8C is a graphical representation of the fraction of cells that were puromycin resistant, thus measuring the polymerase slippage in msh2$^{-/-}$ cells.

DETAILED DESCRIPTION

Figure 1:
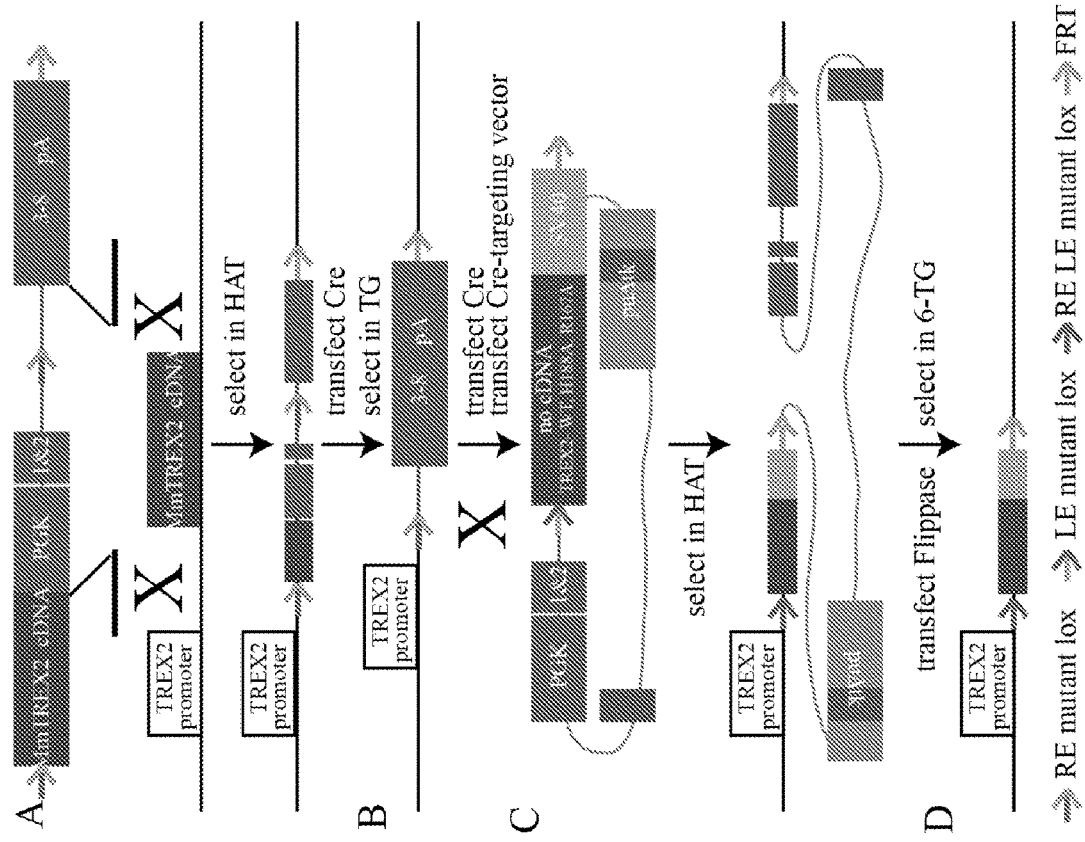
FIG. 1 is a diagrammatic representation of the cloning method undertaken to delete TREX2 in mouse embryonic stem (ES) cells, according to an embodiment.

Reference will now be made to the embodiments illustrated in the drawings, and specific language will be used here to describe the same. It will nevertheless be understood that no limitation of the scope of the disclosure is thereby intended. Alterations and further modifications of the inventive features illustrated here, and additional applications of the principles as illustrated here, which would occur to one skilled in the relevant art and having possession of this disclosure, are to be considered within the scope of the invention.

TREX2 is a 3'→5' exonuclease that removes 3' mismatches in DNA. TREX2 appears to cause chromosomal rearrangements as a participant in a lesion bypass pathway called DNA Damage Tolerance (DDT), also error-free post replication repair. The DDT pathway bypasses lesions at the replication fork (RF) in order to suppress replication fork stalling and collapse. Deletion of TREX2 in mouse embryonic stem (ES) cells defective for either mismatch repair (MMR) or homologous recombination (HR) led to fewer spontaneous mutations. MMR corrects base lesions, mismatches and small insertion/deletions while homologous recombination protects the nascent replication strand from degradation and corrects DNA double strand breaks (DSBs). Both MMR and homologous recombination suppress cancer. TREX2-deletion enhanced cell death in MMR- and HR-defective cells, but not in wild type cells, exposed to certain genotoxins. TREX2-deletion reduced mutations in wild type cells exposed to a variety of genotoxins used for cancer therapy. These attributes make TREX2 an appealing target for cancer therapy. TREX2 knockdown cells derived from human cancer cells show conservation of function.

Embodiments disclosed here also include cellular assays to evaluate TREX2's function. Also disclosed is a genetic system developed in mouse embryonic stem (ES) cells to test the impact of TREX2 on the dose response for chemotherapeutics and for mutagenesis. TREX2-induced mutations in wild type cells and cells defective for MMR (MSH2) and HR (RAD51) were evaluated. Then, dose response assays were conducted to test for cell survival in response to chemotherapeutics. TREX2-deletion increased sensitivity to hydroxyurea (HU) and camptothecin (CPT) for msh2$^{-/-}$ cells and for cells that express defective RAD51$^{K133A}$, respectively.

The innovative cellular assays disclosed here include two classes of reporter systems to detect mutations. One system detects polymerase slippage (when a DNA polymerase slips forward or backward as it transverses a simple nucleotide repeat), and uses one of two reporters, puromycin and green fluorescent protein (GFP) that contain ten adenines $(A)_{10}$ immediately after the translation initiation ATG. Slippage to either 9 or 12 adenines restores the reading frame and results in puromycin resistance or green fluorescence, respectively. MMR corrects polymerase slippage such that msh2$^{-/-}$ cells exhibit a significant increase in the level of puromycin resistant colonies or green fluorescent cells that depend on TREX2. Another system utilizes the HPRT minigene (miniHPRT). HPRT (hypoxanthine phosphoribosyltransferase) is a member of the purine salvage pathway such that HAT (hypoxanthine, aminopterin, thymidine) and TG (6-thioguanine) selection media will select for and against expression, respectively. Thus, TG-resistant colonies score loss of heterozygosity (LOH). MMR-defective and HR-defective cells exhibit a significant increase in TG-resistant colonies that depend on TREX2. Importantly, TREX2-deletion decreased the levels of polymerase slippage mutations and LOH in control cells showing that TREX2 causes mutations in cells with normal DNA repair capacity.

Another embodiment includes a human tissue culture-based system. HCT116 cells were derived from human colon carcinoma and these cells are mutated for MutL Homolog 1 (MLH1), a key component of MMR. TREX2's role in causing polymerase slippage was tested using a GFP reporter [GFP$(A)_{10}$]. About 80% TREX2 knock down with short hairpin RNAs (shRNA) reduced polymerase slippage in HCT116 cells; therefore, our results in mouse cells are relevant to human cancer-derived cells.

TREX2 is an exonuclease that increases genomic instability in both wild type and in DNA repair mutant cells. Deletion of TREX2 will reduce genomic instability in response to cancer therapeutics. TREX2 is instrumental in fusing mismatched repeats during replication to cause palindromic or dicentric chromosomes. TREX2 caused most small mutations and gross chromosomal rearrangements in mouse and human cells defective for a post-replication repair pathway called mismatch repair (MMR) and a replication fork (RF) maintenance pathway called homologous recombination (HR). MMR corrects mismatches and small insertions/deletions while homologous recombination stabilizes stalled RFs and corrects DNA double strand breaks (DSBs) through the annealing of sister chromatids. TREX2-deletion also caused a synthetic phenotype in cells mutated for either MMR or homologous recombination after exposure to either hydroxyurea (HU) or camptothecin (CPT), respectively. TREX2 caused most mutations in in wild type cells exposed to a myriad of genotoxins. These qualities make TREX2 an attractive drug target for cancer therapy. TREX2 causes mutations in p53$^{-/-}$ cells that are defective for stress responses. p53 responds to a variety of stresses including DNA damage and p53$^{-/-}$ cells exhibit increased levels of mutations including aneuploidy. TREX2 inhibitors suppress genomic instability in mouse cells and human cells.

Also described here are embodiments of high-throughput screening methods for TREX2 exonuclease activity. An embodiment of a method of identifying an agent that inhibits exonuclease activity of TREX2 includes the steps of providing an oligonucleotide-based substrate with a reporter associated with 3' end of the oligonucleotide-based substrate and a complementary quencher associated with 5' end of the oligonucleotide-based substrate, followed by incubating the oligonucleotide-based substrate in the presence of TREX2 and a compound under reaction conditions for a sufficient period of time, and then determining amount of reporter disassociated from the oligonucleotide-based substrate. An increase in the amount of reporter disassociated from the oligonucleotide-based substrate relative to control indicates that the compound is an agent that inhibits exonuclease activity of TREX2. In certain embodiments, the oligonucleotide-based substrate can be a single stranded deoxyribonucleic acid. The oligonucleotide-based substrate can be a 20 nucleotide-long single stranded deoxyribonucleic acid. The reporter can be covalently attached to the base of the second to last nucleotide on the 3' end. In certain embodiments, the reporter is located at 25 nucleotides or less from the complementary quencher. The reporter and quencher combination can be Fluorescein and 4'-(4-Nitro-phenyldiazo)-2'-methoxy-5'-methoxy-azobenzene-4"-(N-2-oxy ethyl (4,4' dimethoxy trityl))- N-ethyl-2-cyanoethyl-(N,N-diisopropyl)-phosphoramidite (Black Hole® Quencher). The reporter and quencher combination can be tetramethylrhodamine (TAMRA) and Iowa Black® Red Quencher.

An embodiment of a method of identifying an agent that inhibits exonuclease activity of TREX2 includes a fluorescence-based screening assay, which is preferred for high-throughput screening, as fluorescence detection is very sensitive and requires low concentrations of the fluorescent substrate and the protein. TREX2 is a 3'→5' exonuclease that cleaves single-stranded deoxyoligonucleotides and 3' overhangs. The crystal structure of the substrate-bound TREX2 reveals that the nuclease requires an unmodified 3' hydroxyl, but it is not sequence specific and makes few contacts with the base of the 3' nucleotide, thus the base-attached fluorescent label does not block hydrolysis. So, a 20nt-long ssDNA oligonucleotide was designed with a dark quencher covalently attached to the 5' hydroxyl and a fluorescence tag, such as a fluorescein group, covalently attached to the base of the second to last nucleotide on the 3' end. Fluorescence is quenched in the intact substrate, but when the substrate is cleaved and the fluorescence tag is released, the fluorescence intensity increases. Base attachment of the fluorescence tag is used to prevent interference of the label with the enzymatic activity of TREX2. In an embodiment, the assay displayed high sensitivity and linearity and allowed performing a reading of a 384-well plate in less than two minutes at substrate concentration of 10 nM of TREX2.

Assays as described here were used to screen a Chembridge Diverset library (30,000 compounds). Nineteen small molecules were isolated and five of these were found to reduce a range of mutations to mouse embryonic stem (ES) cells. These small molecules are: 4-benzoyl-2-methyphenyl (2-nitrophenoxy) acetate; N-benzyl-2-([bis(furan-2-yl)-1,2,4-triazin-3-yl] sulfanyl) acetamide; 6-(benzylcarbamoyl)-1-methycyclohex-3-ene-1-carboxylic acid; 8-(phenylamino) naphthalene-1-sulfonic acid; and benzyl 6-(furan-2-yl)-3-methyl-4-oxo-4,5,6,7-tetrahydro-1H-indole-2-carboxylate. These TREX2 inhibitors (TX2Is) do not appear to have an adverse effect on the cells and TREX2-deleted mice do not exhibit a spontaneous phenotype for at least two years (TREX2-null mice have not been observed longer). TX2Is appear to be nontoxic to cells and TREX2-deletion was asymptomatic for >50% of life span. Hence, temporary TREX2-depletion should be safe, and a temporary decrease of TREX2 should not cause problems.

These TREX2 inhibitors are useful as an adjuvant therapy in the treatment of various cancers. These TREX2 inhibitors enhance the chemotherapy or radiation induced cell death of tumor cells with defective DNA repair mechanisms and prevent incidental damage to healthy cells in the body. Chemotherapy and radiation target the quickly replicating tumor cells. However, they also induce damage in healthy cells that are still actively growing and dividing, such as stomach and intestinal epithelial cells, hair follicles, and bone marrow cells. This damage is responsible for many of the severe side-effects of treatment (hair loss, diarrhea, anemia, and fatigue). TREX2 enhances genomic instability in healthy cells, particularly during exposure to agents that damage the DNA (genotoxins). Inhibiting TREX2 results in a reduction of damage from the genotoxic agents. TREX2 inhibitors, when added as an adjuvant to other cancer therapies, have several advantages. The inhibitors act as chemosensitizing agents to enhance the effect of the cancer therapy agents, and thus, enabling the death of the tumor cells at a much lower dose. The inhibitors also act as chemoprotective agents to prevent the damage from the cancer treatments to healthy cells. The TREX2 inhibitors reduce the side-effects caused by the death of healthy cells and mutations induced in surviving healthy cells. The increased efficacy at lower doses of therapies enabled by the TREX2 inhibitors allow a more complete eradication of the tumor cells, thus reducing the chance of future tumors.

Embodiments disclosed here are novel TREX2 inhibitors (TX2Is) that suppress the secondary mutations arising from cancer therapy. Reducing mutations in cancer cells will suppress drug resistance and in wild cells will assist homeostasis and reduce the risk for secondary cancer. TREX2 inhibitors can be used to enhance the effectiveness of cytotoxic cancer drugs and to reduce the level of mutations these drugs cause to normal cells that can lead to side effects like secondary cancers. Furthermore, TREX2 inhibitors could be applied to any catastrophe that includes an exposure to DNA damaging agents such as solar radiation for astronauts, nuclear plant meltdowns like those in Chernobyl and Fukushima, and chemical weapons like mustard gas that were used during World War 1 and in Iraq. Examples of TX2Is disclosed here include 4-benzoyl-2-methyphenyl (2-nitrophenoxy) acetate; N-benzyl-2-([bis(furan-2-yl)-1,2,4-triazin-3-yl] sulfanyl) acetamide; 6-(benzylcarbamoyl)-1-methycyclohex-3-ene-1-carboxylic acid; 8-(phenylamino) naphthalene-1-sulfonic acid; and benzyl 6-(furan-2-yl)-3-methyl-4-oxo-4,5,6,7-tetrahydro-$^1$H-indole-2-carboxylate.

Embodiments include methods of use of TX2Is to suppress mutations in cancer cells to prevent or manage drug resistance and metastasis, and to suppress mutations in wild type cells to maintain homeostasis and suppress secondary cancers. TX2Is are utilized as synthetic agents to kill cancer cells while leaving wild type cells unscathed in response to therapy. TREX2 influences DNA damage tolerance (DDT). DDT maintains replication forks through two branches to bypass lesions. The first is trans-lesion synthesis that bypasses lesions simply by changing a high fidelity polymerase to a translesion synthesis (TLS) polymerase. The second is template switch (TS) that bypasses the lesion with a strand annealing mechanism. The proliferating cell nuclear antigen (PCNA) ubiquitination controls both branches. TLS and TS require mono- and poly-ubiquitination of PCNA K164. The enzyme complex (E2/E3) is the active ligase that transfers the ubiquitin moiety to the target. RAD6/RAD18 is the E2/E3 responsible for monoubiquitination and UBC13/MMS-RAD5 is the E2/E3 responsible for polyubiquitination. In mammals, helicase-like transcription factor (HLTF) and SNF2 Histone-linker PHD-finger RING-finger Helicase (SHPRH) are functional orthologs to RAD5. TREX2 associates with UBC13 and that association increased after exposure to UV light. TREX2-deleted cells were deficient in PCNA mono- and polyubiquitination. TREX2-deleted cells and RAD18-deleted cells exhibited increase levels of stalled RFs in response to hydroxyurea (HU) and were deficient in fusing mismatched repeats. TREX2 participates in both aspects of DDT. TLS and TS cause small mutations and gross chromosomal rearrangements. MMR suppresses the TLS and homologous recombination suppresses TS. For TLS, TREX2 enables RAD18/RAD6 PCNA monoubiquitination that is essential for replacing pol δ with a translesion polymerase (tlp) that can be mutagenic and cause small mutations. For TS, TREX2 enables UBC13/MMS2/RAD5 (HLTF/SHPRH)-mediated PCNA polyubiquitination. TREX2 exonuclease activity is also important for TS and can cause gross chromosomal rearrangements at non-allelic repeats.

TREX2 caused a large number of genomic mutations in wild type cells and in cells defective for MMR and HR. TREX2-deletion reduced spontaneous and genotoxin-induced mutations in mouse ES cells defective for HR or MMR. TREX2-deletion also reduced genotoxin-induced mutations in wild type mouse ES cells. In addition, TREX2-deletion enhanced sensitivity of DNA repair defective ES cells, but not wild type ES cells, to certain genotoxic chemotherapeutics. These results suggest that TREX2 is a good target for cancer therapy as its removal lowered mutations and enhanced killing of cancer cells in response to chemotherapy. The genomic instability results were reproduced in human cancer-derived cells that expressed TREX2 shRNA. Based on these results, TREX2 was chosen as a target for cancer therapy, and small molecule TX2Is were screened for inhibitory activity.

Also, disclosed here are methods of measuring TREX2 levels in bodily fluids and utilizing the expression levels as a prognostic marker and a predictive marker. Based on data from gastric cancer and lung cancer patients, high TREX2 levels significantly correlated with poorer survival. And surprisingly, in breast and ovarian cancer, high TREX2 levels significantly correlated with better survival. A reason for this difference may be that TREX2 inhibits replication fork stalling in parallel with mismatch repair (MMR), so a mutation in these processes additively increases replication fork stalling. By contrast, TREX2 causes replication fork stalling in cells with defective homologous recombination (HR). Persistently stalled replication forks can lead to collapse that can lead to cell death/senescence. TREX2-enabled replication fork restart could assist in cell survival in MMR-defective cells, but TREX2-enabled replication fork stalling could lead to collapse and cell death/senescence in HR-defective cells. This possibility correlates with genetic data that shows MMR defects lead to gastrointestinal cancers and lung cancers while HR defects lead to breast and ovarian cancers. Hence, the TREX2 response would be favorable to cell survival for MMR-impaired cells to enhance cancer development and progression but be unfavorable to cell survival for HR-impaired cells to diminish cancer development and progression.

As used here, the following terms may have the following definitions:

A "pharmaceutical composition" refers to a mixture of two or more of the compounds described herein, or a pharmaceutically acceptable salt, solvate, hydrate or prodrug thereof as an active ingredient. The pharmaceutical composition can also include at least one pharmaceutically acceptable carrier or excipient. The purpose of the pharmaceutical composition is to facilitate administration of a TX2I to a subject. In some embodiments, the pharmaceutical composition includes two or more pharmaceutically acceptable carriers and/or excipients.

The term "pharmaceutically acceptable derivative" as used herein refers to and includes any pharmaceutically acceptable salt, pro-drug, metabolite, ester, ether, hydrate, polymorph, solvate, complex, and adduct of a compound described herein which, upon administration to a subject, is capable of providing (directly or indirectly) the active ingredient. For example, a pharmaceutically acceptable derivative of a TX2I includes all derivatives of the TX2I (such as salts, pro-drugs, metabolites, esters, ethers, hydrates, polymorphs, solvates, complexes, and adducts) which, upon administration to a subject, are capable of providing (directly or indirectly) the TX2I.

As used herein, the term "pharmaceutically acceptable salt" refers to those salts of a compound, which retain the biological effectiveness and properties of the parent compound. And unless otherwise indicated, a pharmaceutically acceptable salt includes salts of acidic or basic groups, which may be present in the compounds disclosed here. Certain embodiments relate to pharmaceutically acceptable salts formed by the compounds described here, their derivatives, their analogs, their tautomeric forms, their stereoisomers, their polymorphs, and pharmaceutically acceptable compositions containing them. Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenylsubstituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methyl benzoate, o-acetoxybenzoate, naphthalene-2-benzoate, bromide, isobutyrate, phenyl butyrate, beta-hydroxybutyrate, chloride, cinnamate, citrate, formate, fumarate, glycolate, heptanoate, lactate, maleate, hydroxymaleate, malonate, mesylate, nitrate, oxalate, phthalate, phosphate, monohydro genphosphate, dihydrogenphosphate, metaphosphate, pyrophosphate, propionate, phenylpropionate, salicylate, succinate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like.

Embodiments of the invention include pharmaceutical compositions containing a TX2I, or a pharmaceutically acceptable salt thereof, and a pharmaceutically acceptable carrier or excipient. Pharmaceutically acceptable ingredients, such as excipients, diluents, fillers, binders, and carriers can be inert or actively contribute to the delivery and distribution of the compounds described here. The formulations used in embodiments here include excipients, such as microcrystalline cellulose, lactose monohydrate, hydroxypropyl cellulose, croscarmellose sodium and magnesium stearate, preferably at least about 50 weight percent (wt %), such as in the range from about 50 wt % to about 95 wt %, including the range from about 50 wt % to about 90 wt %, and more preferably in the range from about 55 wt % to about 85 wt %, such as in the range from about 60 wt % to about 85 wt %, or in the range from about 65 wt % to about 80 wt %, including about 60 wt %, about 65 wt %, about 70 wt %, about 75 wt %, or about 80 wt %.

As used herein, unless otherwise noted, the terms "treating", "treatment" and the like, shall include the management and care of a subject or patient (preferably mammal, more preferably human) for the purpose of combating a disease, condition, or disorder and includes the administration of the compounds of the present disclosure to prevent the onset of the symptoms or complications or alleviate the symptoms or complications.

The term "therapeutically effective amount" as used here, means that amount of active compound or pharmaceutical agent that elicits the biological or medicinal response in a tissue system, animal, or human that is being sought by a researcher, veterinarian, medical doctor or other clinician, which includes a reduction in symptoms or partial or complete recovery from cancer. Compositions for administration herein may form solutions, suspensions, tablets, pills, capsules, sustained release formulations or powders. Illustratively, an effective amount of the compositions described here can range from nanogram/kg to microgram/kg to milligram/kg amounts for young children and adults. Equivalent dosages for lighter or heavier body weights can readily be determined. The dose should be adjusted to suit the individual to whom the composition is administered and will vary with age, weight and metabolism of the individual. The exact amount of the composition required will vary from subject to subject, depending on the species, age, weight and general condition of the subject, the particular a TX2I used, its mode of administration and the like. An appropriate amount can be determined by one of ordinary skill in the art using only routine experimentation given the teachings herein. One skilled in the art will realize that dosages are best optimized by the practicing physician or veterinarian and methods of determining dose amounts and regimens and preparing dosage forms are described, for example, in Remington: The Science and Practice of Pharmacy, 22nd edition or Goodman & Gilman's The Pharmacological Basic of Therapeutics, 12th edition; the Merck Manual, Professional Version.

Embodiments include a therapeutically effective pharmaceutical composition containing 4-benzoyl-2-methyphenyl (2-nitrophenoxy) acetate, or pharmaceutically acceptable derivatives thereof. Embodiments also include methods of increasing effectiveness of a chemotherapeutic agent in a mammalian cancer cell, whereby the therapeutically effective pharmaceutical composition containing 4-benzoyl-2-methyphenyl (2-nitrophenoxy) acetate, or pharmaceutically acceptable derivatives thereof, is administered to the mammalian cancer cell exposed to the chemotherapeutic agent.

Embodiments include a therapeutically effective pharmaceutical composition containing N-benzyl-2-([bis(furan-2-yl)-1,2,4-triazin-3-yl] sulfanyl) acetamide, or pharmaceutically acceptable derivatives thereof. Embodiments also include methods of increasing effectiveness of a chemotherapeutic agent in a mammalian cancer cell, whereby the therapeutically effective pharmaceutical composition containing N-benzyl-2-([bis(furan-2-yl)-1,2,4-triazin-3-yl] sulfanyl) acetamide, or pharmaceutically acceptable derivatives thereof, is administered to the mammalian cancer cell exposed to the chemotherapeutic agent.

Embodiments include a therapeutically effective pharmaceutical composition containing 6-(benzylcarbamoyl)-1-methycyclohex-3-ene-1-carboxylic acid, or pharmaceutically acceptable derivatives thereof. Embodiments also include methods of increasing effectiveness of a chemotherapeutic agent in a mammalian cancer cell, whereby the therapeutically effective pharmaceutical composition containing 6-(benzylcarbamoyl)-1-methycyclohex-3-ene-1-carboxylic acid, or pharmaceutically acceptable derivatives thereof, is administered to the mammalian cancer cell exposed to the chemotherapeutic agent.

Embodiments include a therapeutically effective pharmaceutical composition containing 8-(phenylamino)naphthalene-1-sulfonic acid, or pharmaceutically acceptable derivatives thereof. Embodiments also include methods of increasing effectiveness of a chemotherapeutic agent in a mammalian cancer cell, whereby the therapeutically effective pharmaceutical composition containing 8-(phenylamino)naphthalene-1-sulfonic acid, or pharmaceutically acceptable derivatives thereof, is administered to the mammalian cancer cell exposed to the chemotherapeutic agent.

Embodiments include a therapeutically effective pharmaceutical composition containing benzyl 6-(furan-2-yl)-3-methyl-4-oxo-4,5,6,7-tetrahydro-1H-indole-2-carboxylate, or pharmaceutically acceptable derivatives thereof. Embodiments also include methods of increasing effectiveness of a chemotherapeutic agent in a mammalian cancer cell, whereby the therapeutically effective pharmaceutical composition containing benzyl 6-(furan-2-yl)-3-methyl-4-oxo-4,5,6,7-tetrahydro-1H-indole-2-carboxylate, or pharmaceutically acceptable derivatives thereof, is administered to the mammalian cancer cell exposed to the chemotherapeutic agent.

EXAMPLES

Example 1

FIG. 1 is a diagrammatic representation of the cloning method undertaken to delete TREX2 in mouse ES cells. TREX2 is on the X chromosome, so only one copy needs to be deleted in XY cells. The HPRT (hypoxanthine phosphoribosyl-transferase) minigene (miniHPRT) was used for selection. The clones were selected for the presence of miniHPRT in HAT (hypoxanthine, aminopterin, thymidine) and for its absence in 6-thioguanine (6-TG). A loxP and the MmTREX2 cDNA was present 5' to miniHPRT and a second loxP was present in the intron. The recombinant mutant lox was in the intron (red green arrow) and another RE mutant lox flanked the 5' region. A short flippase recognition target (FRT) was placed at the 3' end of miniHPRT. Correct recombinant clones were identified by PCR screening. The loxP and MmTREX2 cDNA were then deleted with Cre-recombinase and selected in 6-TG (FIG. 1B). Using a knock-in protocol, an empty vector or human TREX2 wild type (WT) or HsTREX2 mutated for its exonuclease activity (H188A) or its DNA binding activity (R167A) was inserted (FIG. 1C). The Cre-mediated targeting vector contained the 5' half of miniHPRT, an LE mutant lox (green red arrow), a FRT and the cDNA. HAT was used to select for miniHPRT restoration, and PCR was used to screen for the positive clones. These cells were used for further experimentation. Further manipulation of these cells also included the removal of the backbone, miniHPRT, and the puromycin N-acetyltransferase delta 1 thymidine kinase (puΔtk) recombinant substrate using flippase (FIG. 1D). Flippase was transfected into the cells to remove the backbone, a FRT, puΔtk, and miniHPRT. These cells were selected in 6-TG.

Example 2

Figure 2:
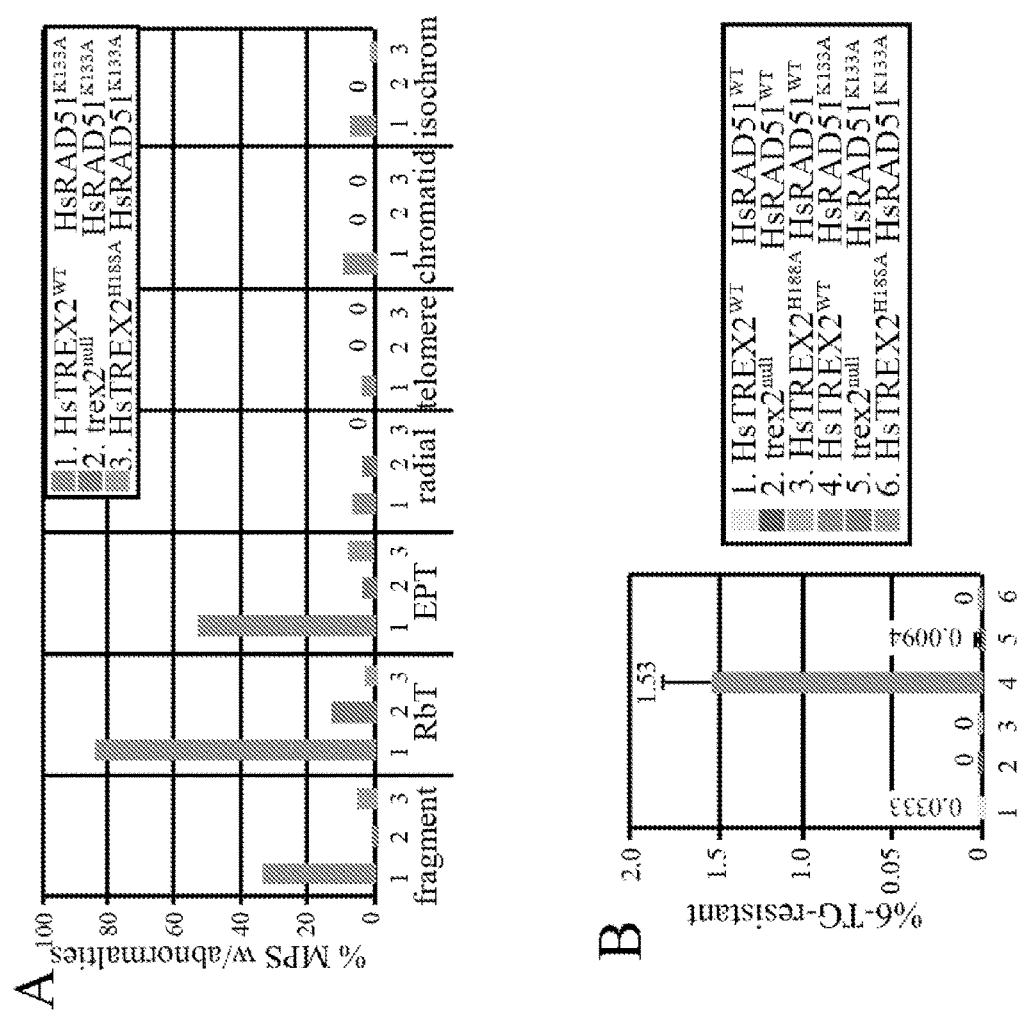
FIGS. 2A and 2B are graphical representations showing the effects of TREX2 causing gross chromosomal rearrangements and loss of heterozygosity respectively in HsRAD51$^{K133A}$ (KA) cells, according to an embodiment.

TREX2 function was evaluated in cells defective for HR. Homologous recombination maintains replication fork integrity and repairs DNA double strand breaks at the replication fork. Defects in homologous recombination predispose individuals to breast and ovarian cancer. Using a knockout-knockin protocol, TREX2 and then RAD51 were altered in animal cells as described here. RAD51 is central to homologous recombination, and is a recombinase that binds to single strand gaps and the 3' end at a double strand break to initiate double strand break repair by annealing to the homologous sequence on the sister chromatid. Using this knockout-knockin system, HsRAD51$^{WT}$ and HsRAD51$^{K133A}$ were introduced into cells that contained HsTERX2$^{WT}$ or empty vector (trex2$^{null}$), or HsTREX2$^{H188A}$ (deleted for exonuclease activity). HsRAD51$^{K133A}$ is not able to bind ATP in the conserved Walker A motif. FIGS. 2A and 2B are graphical representations of the effects of TREX2 causing gross chromosomal rearrangements and loss of heterozygosity of the HPRT minigene (miniHPRT), respectively in HsRAD51$^{K133A}$ (KA) cells. TREX2 caused gross chromosomal rearrangements in HsRAD51$^{K133A}$ cells. To observe gross chromosomal rearrangements, two-color fluorescence in situ hybridization (FISH) was performed on metaphase phase spreads. Metaphase spreads from these cells were stained with a telomeric probe (green), a MSR probe in the pericentromere (red) and counterstained with DAPI (blue). The HsRAD51$^{K133A}$ expressing cells with HsTREX2$^{WT}$ (lane 1, green) were compared to trex2$^{null}$ (lane 2, red) and HsTREX2$^{H188A}$ (lane 3, blue). The average of three biological replicates are presented (p<0.0001 for lane 1 versus lanes 3 and 4 for EPT and RbT, using student T test). Cells expressing HsRAD51$^{K133A}$/HsTREX2$^{WT}$ exhibited 1.9 abnormalities per metaphase spread (142/74) (FIG. 2A). By contrast HsRAD51$^{K133A}$/trex2$^{null}$ exhibited 0.19 abnormalities per metaphase spread (16/83) (FIG. 2A) and HsRAD51$^{K133A}$/HsTREX2$^{H188A}$ exhibited 0.024 abnormalities per metaphase spread (7/46) (FIG. 2A). That is a 10- to 79-fold decrease. TREX2-deletion reduced spontaneous and genotoxin-induced mutations in mouse ES cells defective for homologous recombination.

To evaluate loss of heterozygosity, the loss of function (LOF) of miniHPRT was measured by survival in 6-TG. ES cells were grown in 1× hypoxanthine, aminopterin, thymidine (HAT) for at least 4 days followed by growth in 1× HT for 2 days and then no selection for 1 day. Cells were counted and seeded at 2×10$^5$ cells/10 cm feeder plates (3 plates) and selected in 10 µM 6-thioguanine (6-TG). For plating efficiency, 2000 cells were seeded on two wells of 6-well feeder plate. Eight days after plating, the number of 6-TG resistant colonies was counted. Cells expressing HsRAD51$^{K133A}$/HsTREX2$^{WT}$ exhibited 1.5% 6-TG-resistant colonies (FIG. 2B). By contrast, HsRAD51$^{K133A}$/trex2$^{null}$ exhibited 0.0094% 6-TG-resistant colonies (FIG. 2B) and HsRAD51$^{K133A}$/HsTREX2$^{H188A}$ exhibited 0% 6-TG-resistant colonies (FIG. 2B). That is >159-fold difference. The average of three biological replicates are presented (p<0.0001 for lane 4 versus lanes 5 and 6, unpaired student T test). Deletion of TREX2 in HsRAD51$^{K133A}$ expressing cells reduces loss of heterozygosity to levels lower than in wild type cells. Therefore, TREX2 caused greatest loss of heterozygosity and gross chromosomal rearrangements in HR-defective cells.

Example 3

TREX2 function was observed in cells defective for MMR. MMR corrects polymerase-associated problems including mis-incorporation of bases and polymerase slippage that make small insertions and deletions. MutS homolog complexes, such as MSH2-MSH6 (MutSα) and MSH2-MSH3 (MutSβ), recognize and bind to the defect. MutSα corrects mismatches and small insertions-deletions while MutSβ corrects small insertion-deletions. MLH1-PMS2 (MutLα) binds to MutSα and then PCNA activates MutLα to incise the nascent strand. Defective MMR causes a mutator phenotype. Mutations in MMR genes result in cancers that include hereditary nonpolyposis coli, brain tumors, leukemia, and lymphoma. Deletions in genes that regulate MSH2 degradation were found in sporadic colorectal cancer and in acute lymphoblastic leukemia. MMR-mutant cells are resistant to drugs, especially thiopurines.

Figure 3:
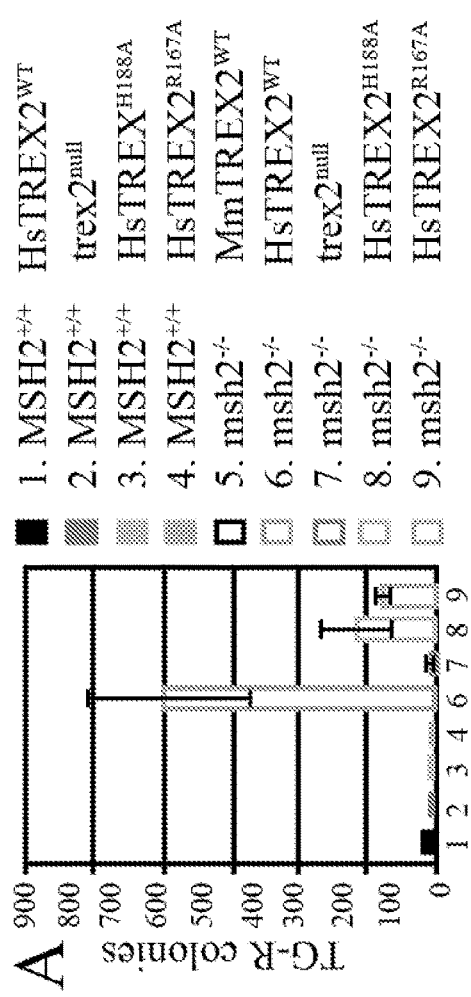
FIGS. 3A and 3B are graphical representations of the analysis of TREX2-caused mutations in mismatch repair (MMR)-mutant cells, according to an embodiment.
Figure 3:
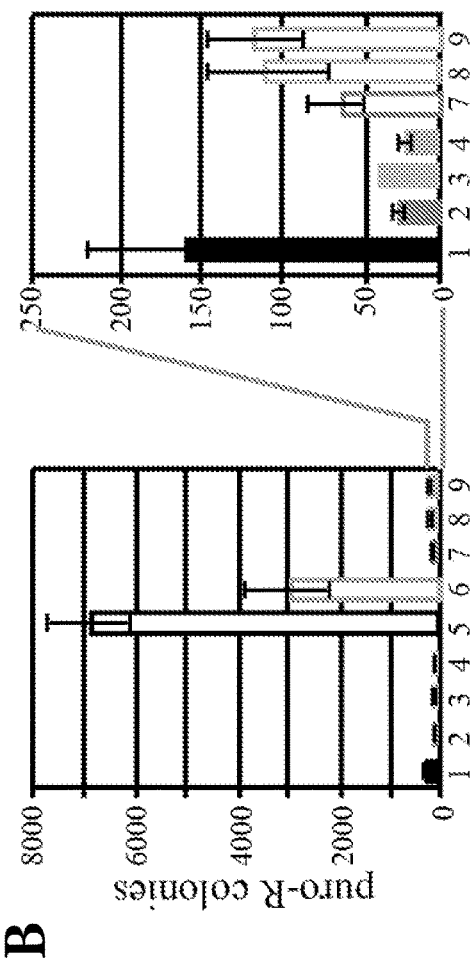

Expression of TREX2 in msh2$^{-/-}$ mouse ES cells was evaluated using the knockout-knockin technology, previously described herein. The expression of an empty vector (trex2$^{null}$) was compared to that of HsTREX2$^{WT}$, HsTREX2$^{H188A}$ and HsTREX2$^{R167A}$ (deleted for DNA binding activity). The mutations were screened with the miniHPRT loss of heterozygosity assay. FIGS. 3A and 3B are graphical representations of the analysis of TREX2-caused mutations in MMR-mutant cells. FIG. 3A is a graph presenting the results of a loss of heterozygosity assay with miniHPRT in msh2$^{-/-}$ mouse ES cells. Polymerase slippage assay with puro(A)$_{10}$ in msh2$^{-/-}$ mouse ES cells and in WT cells. The average of three biological replicates are presented (p<0.0001 for lane 6v7-9, unpaired student T test). Compared to control cells, TREX2-deletion or expression of HsTREX2$^{H188A}$ and HsTREX2$^{R167A}$ reduced the number of 6-TG-resistant colonies (FIG. 3A, compare lane 1 to 2-4). Compared to control cells, MSH2-deletion increased the number of 6-TG-resistant colonies by ~30-fold when expressing HsTREX2$^{WT}$ (FIG. 3A, compare lanes 1 to 6). PCR analysis showed the 6-TG-resistant clones to have small deletions. Compared to msh2$^{-/-}$ cells, trex2$^{null}$ or expression of HsTREX2$^{H188A}$ and HsTREX2$^{R167A}$ reduced 6-TG-resistant colonies (FIG. 3A, compare lanes 6 to 7-9).

TREX2-deletion was almost absolute in msh2$^{-/-}$ cells as there were colonies in these cells as compared to control cells.

The polymerase slippage with a puro(A)$_{10}$ uses a puro-selection cassette with an out of frame (A)$_{10}$ immediately downstream of the initiation ATG to select for polymerase slippage. FIG. 3B is a graph presenting the results of a polymerase slippage assay with puro(A)$_{10}$ in msh2$^{-/-}$ mouse ES cells and in WT cells. The average of three biological replicates are presented (p<0.0001 for lane 5v7-9 and 6v7-9, unpaired student T test). Compared to control cells, TREX2-deletion or expression of HsTREX2$^{H188A}$ and HsTREX2$^{R167A}$ reduced the number of puro-resistant colonies (FIG. 3B, compare lane 1 to 2-4). Compared to control cells, MSH2-deletion increased the number of puro-resistant colonies by ~18 to 45-fold when expressing MmTREX2$^{WT}$ or HsTREX2$^{WT}$, respectively (FIG. 3B, compare lane 1 to 5, 6). As compared to msh2$^{-/-}$ cells, trex2$^{null}$ or expression of HsTREX2$^{H188A}$ and HsTREX2$^{R167A}$ reduced 6-TG-resistant colonies (FIG. 3B, compare lanes 5 and 6 to lanes 7 through 9). TREX2-deletion in msh2$^{-/-}$ cells reduced polymerase slippage to a level lower than that seen in control cells (FIG. 3B, right panel, compare lane 1 to 7-9).

Example 4

Figure 4:
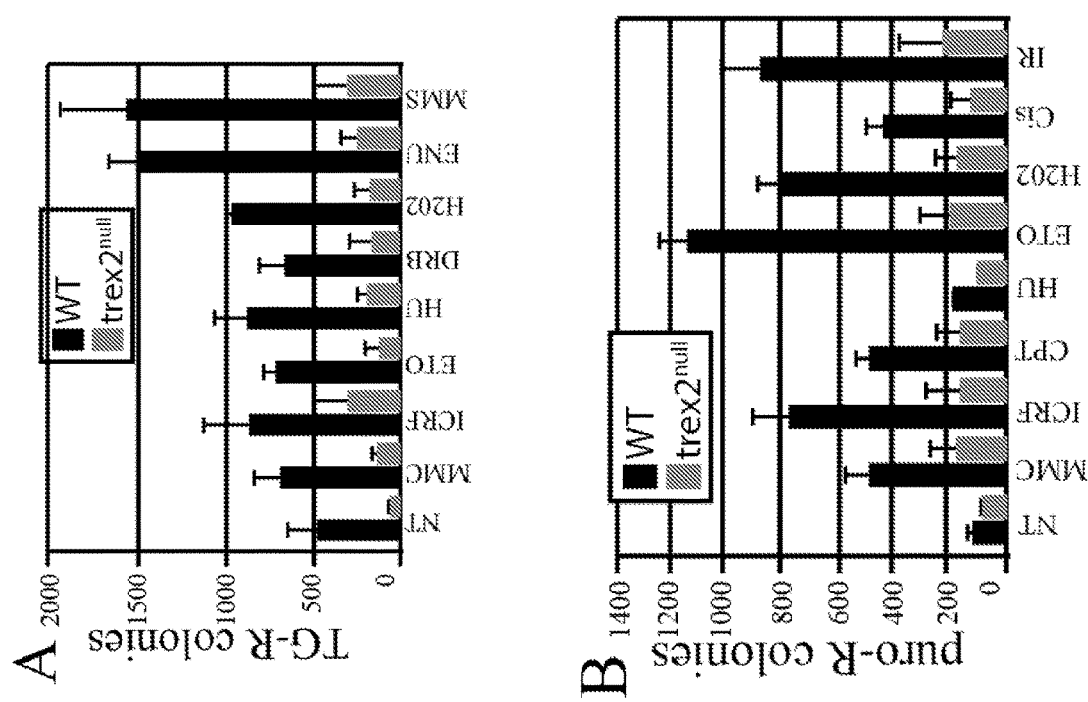
FIGS. 4A and 4B are graphical representations of the effects of TREX2-deletion in cells exposed to genotoxins, according to an embodiment.

TREX2 caused a range of small mutations in MMR-mutant cells (small deletions and polymerase slippage) that is different from HsRAD51$^{K133A}$ expressing cells (big deletion). This could be due to TREX2 influences of both TLS and TS by ubiquitination of PCNA. TREX2-deletion reduced mutations in wild type cells after exposure to genotoxins. FIGS. 4A and 4B are graphical representations of the effects of TREX2-deletion in cells exposed to genotoxins. Exposure to all genotoxins increased mutations in WT cells using both miniHPRT loss of heterozygosity (FIG. 4A) and the puro(A)$_{10}$ (FIG. 4B) assays. The trex2$^{null}$ cells exhibit less loss of heterozygosity with miniHPRT (A) and polymerase slippage with puro(A)$_{10}$ (B) than WT cells exposed to genotoxins. TREX2-deletion negated this increase for all genotoxins, to levels similar or lower than unexposed WT cells (No treatment, NT). These genotoxins include crosslinking agent (MMC, Cis), type 1 topoisomerase inhibitors (CPT), type 2 topoisomerase inhibitors/poisons (ICRF-154, ETO), alkylating agents (ENU, MMS), ribonucleotide reductase inhibitor (HU), hydrogen peroxide (H$_2$O$_2$) and RNA polymerase II inhibitor (DRB). Thus, TREX2-deletion appears to suppress a wide range of lesions caused by a range of genotoxins.

Example 5

Figure 5:
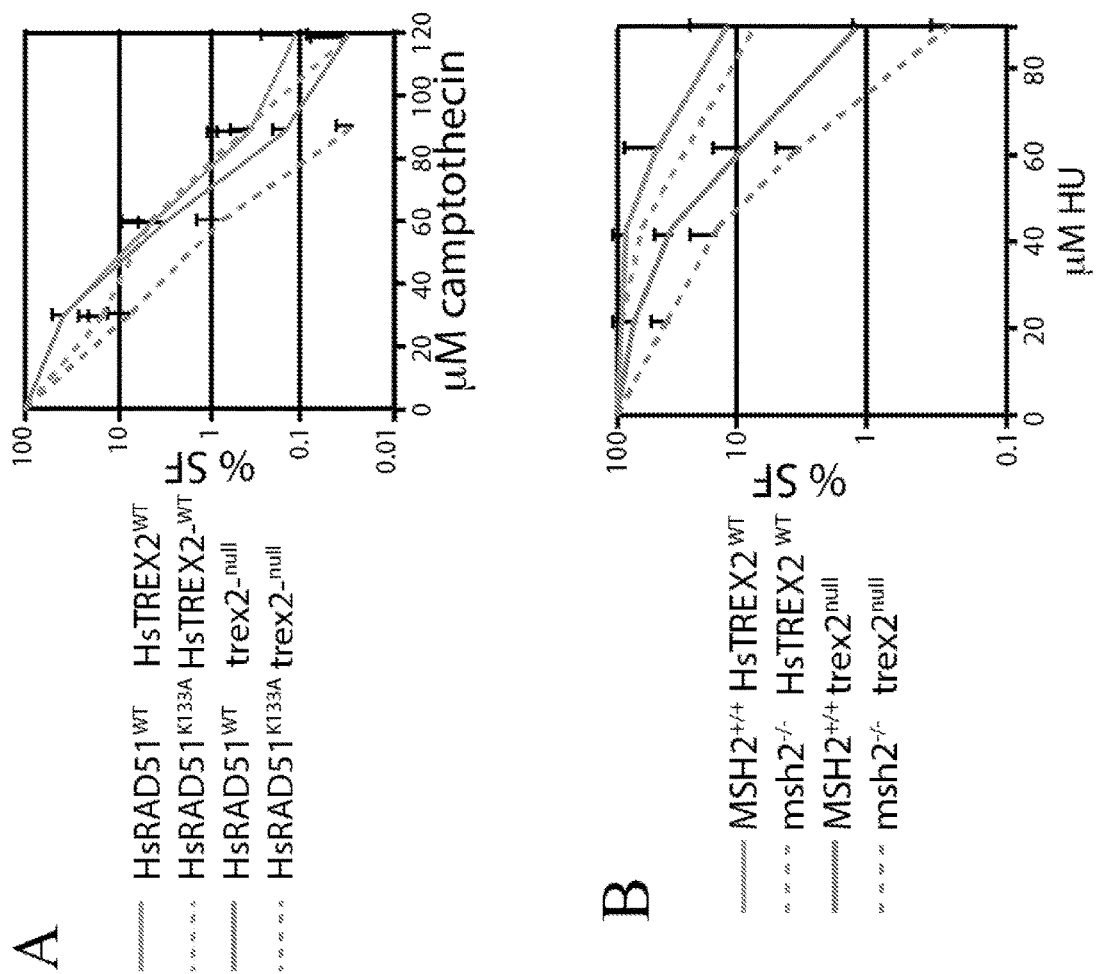
FIGS. 5A and 5B are graphical representations of the effects of TREX2-deletions measured as survival fractions, according to an embodiment.

TREX2-deletion also imparts a synthetic phenotype in HR-mutant and MMR-mutant cells to hydroxyurea (HU) and camptothecin (CPT). Both CPT and HU stall RFs and are used for cancer therapy. CPT binds type 1 topoisomerase II to DNA to cause a break when a replication fork collides into it while HU inhibits ribonucleotide reductase to deplete nucleotides. Therefore, TX2Is enhance cell killing of chemotherapeutic agents in cancer cells while protecting the patient from mutations to reduce the risk of therapy-related disease. RAD51$^{K133A}$ was expressed in mouse ES cells to negatively alter HR. In these HR defective cells, TREX2-deletion decreased survival to camptothecin and reduced loss of heterozygosity (LOH) to levels lower than cells expressing RAD51 wild type (WT) and TREX2 WT. LOH is loss of miniHPRT, which can be scored as resistance to 6-thioguanine (TG). FIGS. 5A and 5B are graphical representations of the effects of TREX2-deletions measured as survival fractions. FIG. 5A shows TREX2-deletions causing synthetic toxicity in HR-mutant cells to CPT (WT/KA v null/KA: 20 µM p=0.007, 90 µM p=0.0058); FIG. 5B shows TREX2-deletions causing synthetic toxicity in MMR-mutant cells to HU (WT/KA v null/KA: 20 µM p=0.007, 40 µM p=0.011, 90 µM p=0.049). The average of three biological replicates are presented.

Example 6

Figure 6:
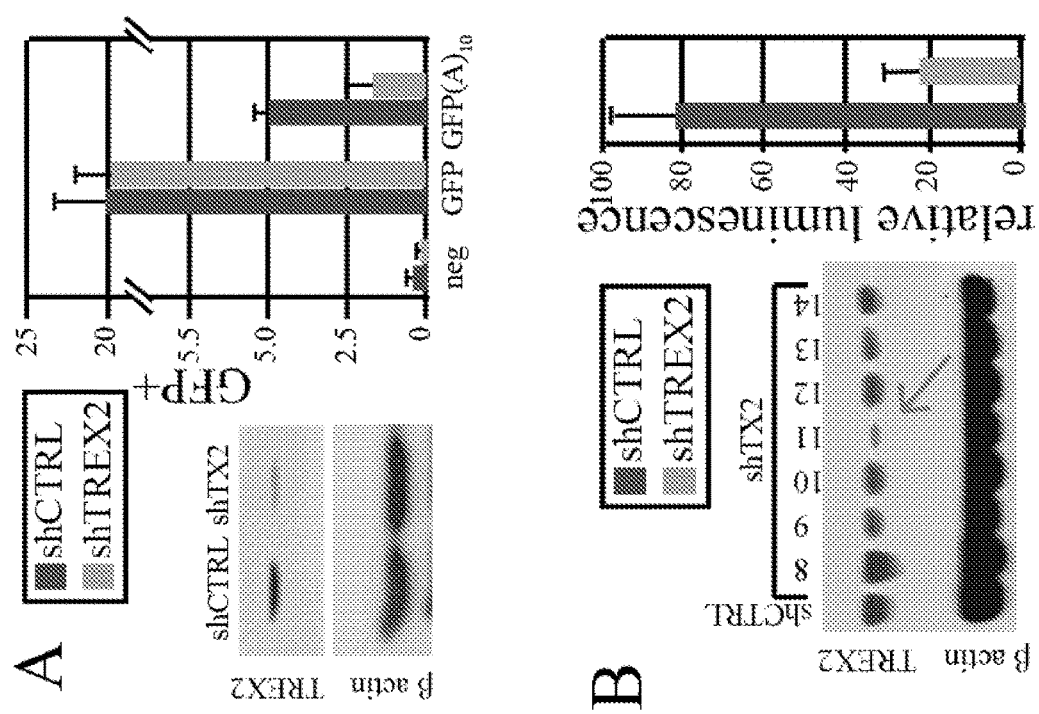
FIGS. 6A, 6B, and 6C are graphical representations of polymerase slippage assays using a frameshift reporter, according to an embodiment.
Figure 6:
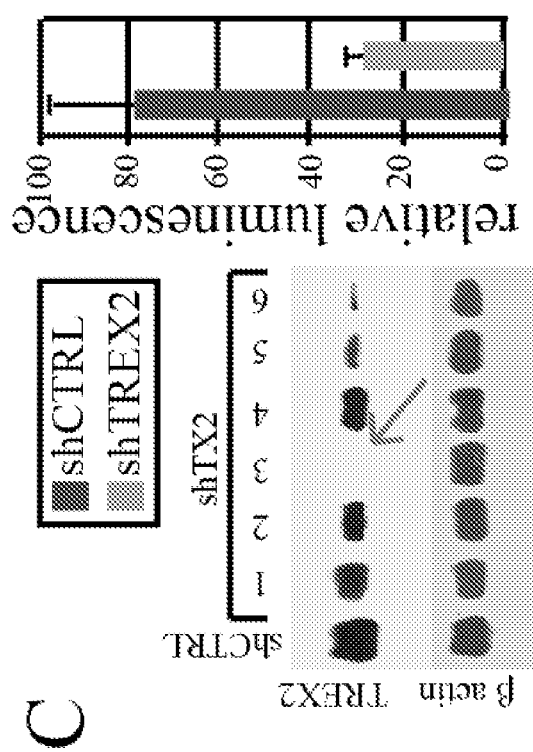

TREX2 caused mutations in human cells as it did in mouse ES cells. TREX2 depletion with shRNA reduced polymerase slippage in MMR-mutant human cancer-derived cells demonstrating that results in mouse cells translate to human cancer cells. FIGS. 6A, 6B, and 6C are graphical representations of polymerase slippage assays using a frameshift reporter. FIG. 6A is a graphical representation of polymerase slippage assay using $GFP(A)_{10}$ as the frameshift reporter in HCT116 cells. These cells were derived from colorectal carcinoma. The average of three biological replicates are presented (p=0.0043 for shTREX2 as compared to shCTRL with $GFP(A)_{10}$, unpaired student T test). FIG. 6B is a graphical representation of polymerase slippage assay using luciferase(A)10 as the frameshift reporter in SKOV3 cells. SKOV3 cells (ATCC® HTB-77™) were transfected with a luciferase$(A)_{10}$ reporter. These cells were derived from ovarian adenocarcinoma. Their growth was not responsive to estradiol and was not inhibited by OH-tamoxifen and ICI. The average of three biological replicates are presented [p=0.0091 for shTREX2 as compared to shCTRL with luciferase$(A)_{10}$, unpaired student T test]. Red arrow points to clone used for transfection in FIG. 6B. FIG. 6C is a graphical representation of polymerase slippage assay using luciferase $(A)_{10}$ as the frameshift reporter in CCRF-CEM cells. TREX2 knockdown reduced polymerase slippage in human MLH1-deficient cells. HCT116 cells (ATCC® CCL247™) were transfected with a $GFP(A)_{10}$ reporter. CCRF-CEM (ATCC® CCL-199™) cells were transfected with a luciferase$(A)_{10}$ reporter. These cells were derived from acute lymphoblastic leukemia. The average of three biological replicates are presented [p=0.0155 for shTREX2 versus shCTRL with luciferase$(A)_{10}$, unpaired student T test] as shown in FIG. 6C. Red arrow points to clone used for transfection in FIG. 6C. All three were mutated for MLH1. Therefore, shRNA of TREX2 appears to impart the same phenotype as a genetic deletion.

Example 7

Figure 7A:
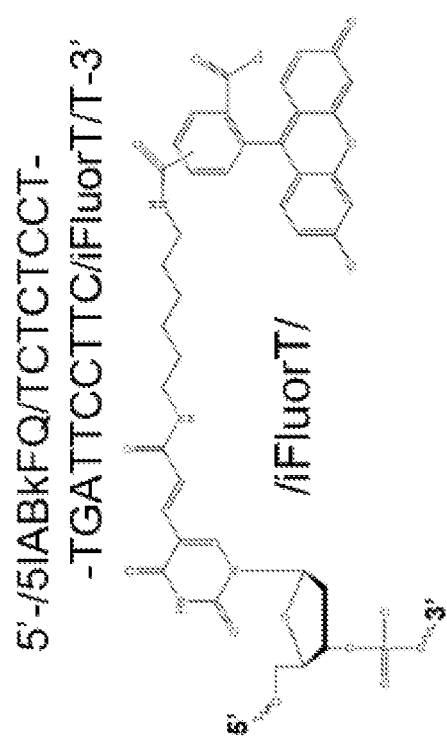
FIG. 7A is an example of a ssDNA oligonucleotide substrate, according to an embodiment.
Figures 7B, 7C:
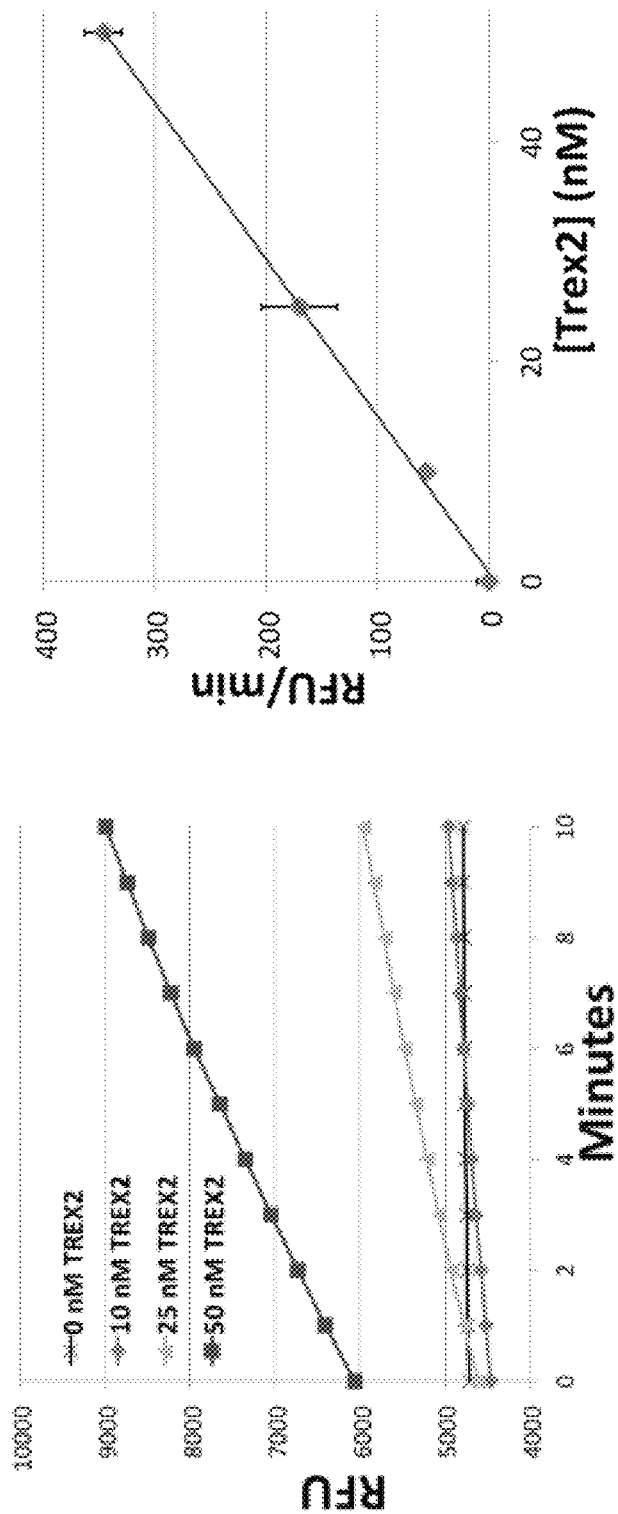
FIG. 7B is a graphical representation of TREX2-catalyzed hydrolysis of the substrate, which is measured as the increase of the fluorescence signal, according to an embodiment.
FIG. 7C is a graphical representation of the hydrolysis rates of the substrate plotted against TREX2 concentration, according to an embodiment.

A twenty nucleotide-long single stranded DNA oligonucleotide (5'-/5IABkFQ/TCTCTCCTTGATTCCTTC/iFluorT/T-3') was designed with a dark quencher covalently attached to the 5' hydroxyl and a fluorescein group covalently attached to the base of the second to last nucleotide on the 3' end, as shown in FIG. 7A. Fluorescence is quenched in the intact substrate, but when the substrate is cleaved and the fluorescein label is released, the fluorescence intensity is increased approximately 7-fold. Base attachment of the fluorescein label is used to prevent interference of the label with the enzymatic activity of TREX2. FIG. 7B is a graphical representation of TREX2-catalyzed hydrolysis of the substrate, which is measured as the increase of the fluorescence signal. Four different concentrations of TREX2 were evaluated. FIG. 7C is a graphical representation of the hydrolysis rates of the substrate plotted against TREX2 concentration. The assay displayed high sensitivity and linearity and allowed performing a reading of a 384-well plate in less than two minutes at substrate concentration of 10 nM.

Example 8

Figure 8A:
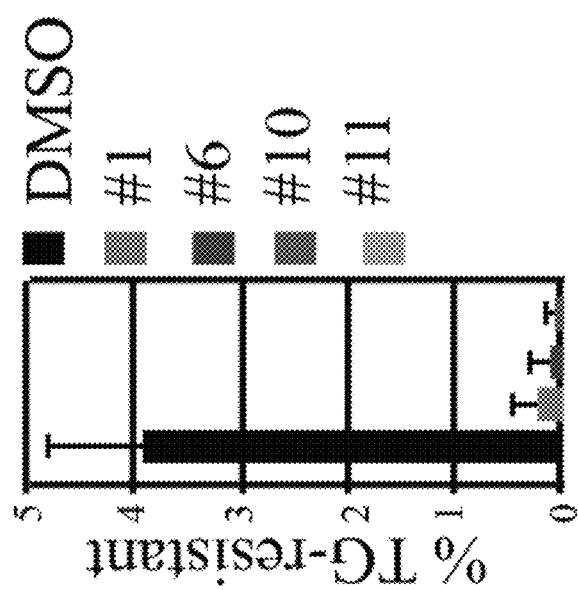
FIGS. 8A, 8B, and 8C show the inhibitory activity of certain TREX2 inhibitors (TX2Is), according to an embodiment.
Figure 8B:
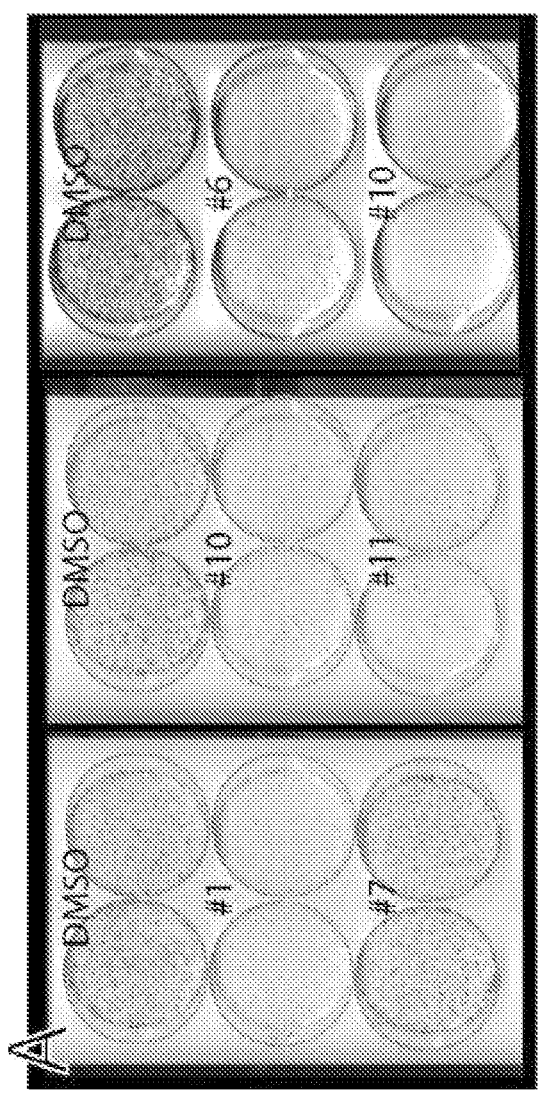
Figure 8C:
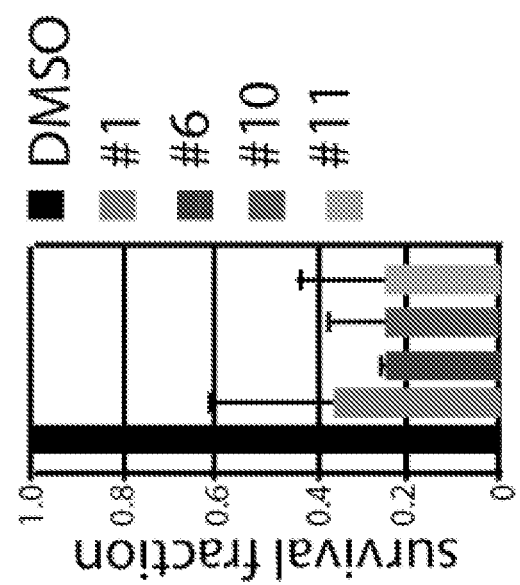

The Chembridge Diverset library with 30,000 small molecules was used in the biochemical assay described in Example 7 that quantitates TREX2's exonuclease activity. Nineteen compounds were isolated. FIGS. 8A, 8B, and 8C show the inhibitory activity of certain TX2Is.

Compounds #1, 6, and 10 reduce LOH in $RAD51^{K133A}$ expressing cells using miniHPRT. FIG. 8A is a graphical representation of the percentage of TG-resistant cells, following the exposure of the $RAD51^{K133A}$ expressing cells to compounds 1, 6, and 10 (Control versus compounds 1/6/10, p<0.018, T test, average of three replicates).

Compounds #1, 6, 10, and 11 reduce spontaneous polymerase slippage in $msh2^{-/-}$ cells using $puro(A)_{10}$ assay, as shown in FIGS. 8B and 8C. FIG. 8B is a photographic image of the plates with puromycin resistant cells. For this experiment, $msh2^{-/-}$ cells that were stably transfected with the puro $(A)_{10}$ reporter were seeded at the same concentration on each well of a 6-well plate (day 0). The next day either vehicle (DMSO) or 10 µM TREX2 inhibitor was added along with puromycin. Colonies were stained and counted on about day 10. Compound 1 is 4-benzoyl-2-methyphenyl (2-nitrophenoxy) acetate. Compound 6 is 8-(phenylamino) naphthalene-1-sulfonic acid. Compound 10 is N-benzyl-2-([bis(furan-2-yl)-1,2,4-triazin-3-yl] sulfanyl) acetamide and Compound 11 is 6-(benzylcarbamoyl)-1-methycyclohex-3-ene-1-carboxylic acid. FIG. 8C is a graphical representation of the fraction of cells that were puromycin resistant, thus measuring the polymerase slippage in $msh2^{-/-}$ cells (DMSO versus compounds 1/6/10/11: p<0.02, student T test, average of three replicates).

Example 9

DDT is a pathway that suppresses RF stalling and collapse but is prone to generating mutations. There are two branches. The first is trans-lesion synthesis (TLS) that bypasses lesions by changing a high fidelity replicative polymerase with TLS polymerase, some of which have low fidelity. The second is template switch (TS) that bypasses lesions via a poorly understood strand exchange mechanism. This mechanism should be high fidelity, but if strand annealing occurs with a non-allelic template, a rearrangement can occur. The consequences of altering members of the DDT pathway were evaluated in WT and msh2−/− cells, which include interactions with PCNA, RAD18, UBC13, HLTF and SHPRH. Both spontaneous and genotoxin-induced mutations were measured.

TREX2 associated by GST was pulled down with PCNA, RAD18, UBC13, HLTF and SHPRF (not shown) and by co-immunoprecipitation with UBC13 and SHPRH. RAD18, UBC13, HLTF and SHPRH ubiquitinate PCNA. SHPRH and HLTF are functional orthologs to yeast RAD5 and they coordinate post replication lesion bypass in response to different types of damage. HLTF suppressed UV-induced mutations, while SHPRH suppressed MMS-induced mutations using a plasmid-based mutation assay. This assay used a plasmid encoding a suppressor tRNA that was damaged with UV or MMS and transfected into human cells along with siRNA to either HLTF or SHPRH. The plasmid was replicated and then transformed into *E. coli* containing a lacZ gene with a premature stop codon. Mutation frequency was evaluated by color selection. HLTF and SHPRH utilize high fidelity TLS polymerases.

Figure 9:
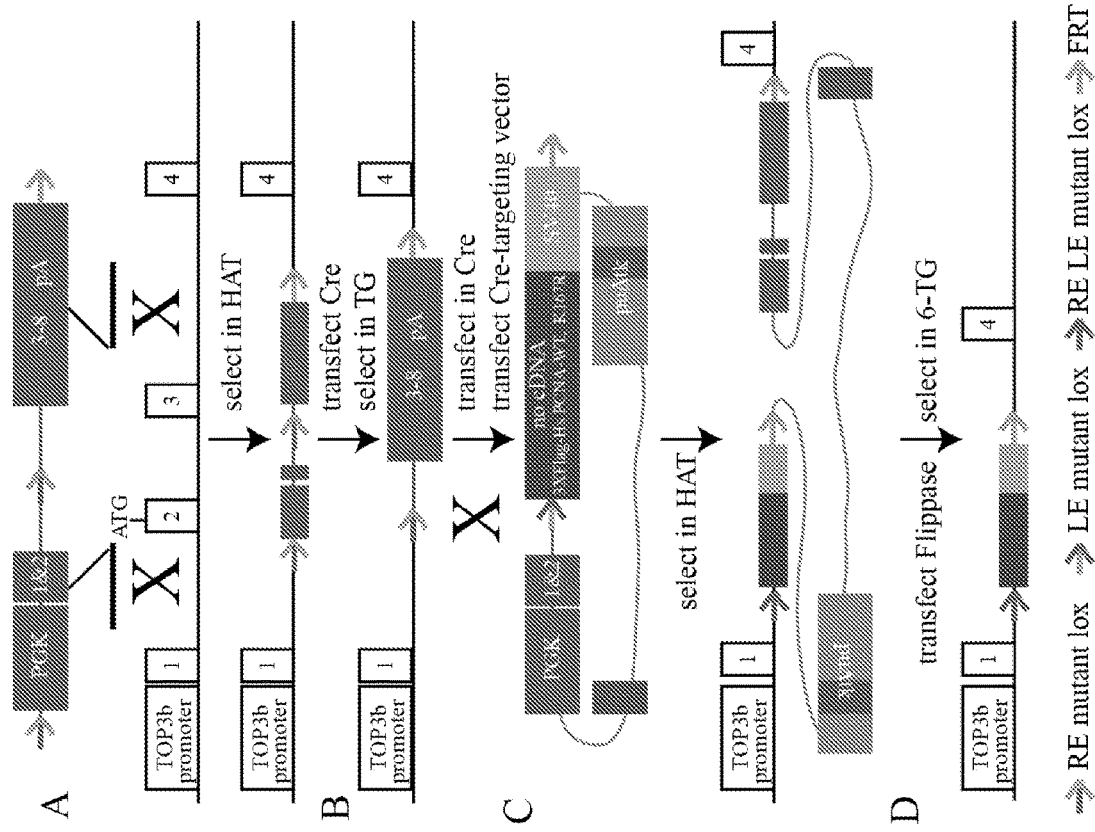
FIG. 9 is a diagrammatic representation of a high throughput knockin protocol at TOP3β with the integration of the puΔtk recombination substrate, according to an embodiment.

Described in FIG. 9 is a high throughput knockin protocol at TOP3β with the integration of the puΔtk recombination substrate. The TOP3β exons 2 & 3 were replaced with miniHPRT. A RE mutant loxP was presented in the intron (red green arrow) and another RE mutant lox flanks the 5' end. An FRT was presented at the 3' end of miniHPRT (blue arrow). Clones were selected in HAT (hypoxanthine, aminopterin, thymidine) and the targeting was confirmed by PCR screening. The 5' half of miniHPRT and a RE mutant lox were removed by Cre-mediated recombination. Clones were selected in 6-TG and the targeting was confirmed by PCR screening. An empty vector or 3XFlag-HsPCNA$^{Wt}$ or 3XFlag-HsPCNA$^{K164R}$ was knocked-in by Cre-mediated recombination. The Cre-mediated targeting vector contained the 5' half of miniHPRT, an LE mutant lox (green red arrow), a FRT and the cDNA. Clones were selected in HAT (hypoxanthine, aminopterin, thymidine) and the targeting was confirmed by PCR screening. The puΔtk recombination cassette was the backbone. Flippase was transfected in to remove the backbone, a FRT, puΔtk and miniHPRT. Clones were selected in 6-TG and the targeting was confirmed by PCR screening. A gRNA-CRISPR-Cas9 can be used to delete the expression of the remaining DDT genes (RAD18, UBC13, HLTF and SHPRH) in WT and msh2$^{-/-}$ cells that are targeted at TOP3β with miniHPRT (FIG. 9A). Cre recombinase plus two-three gRNA-CRISPR-Cas9 can be co-transfected into cells with floxed miniHPRT (FIG. 9B). The Cre recombinase will excise miniHPRT rendering the cells resistant to 6-TG and providing selection for transfected cells as shown in FIG. 9C. Then 6-TG cells can be picked and tested for a mutation using PCR primers that flank the region subject to gRNA-induced cutting. Two-three gRNAs can be used for easy detection. Altered-size PCR fragments can be sequenced to ensure a mutation. This approach has worked for knocking-out RAD18. Two mutated clones can be used to avoid evaluation of off-target effects and the phenotype can be rescued with cDNA. Once a mutant clone has been generated, an empty vector can be knocked-in as shown in FIG. 9D and a vector with the cDNA to the gene that was mutated can be knocked-in as a control. This means that all clones will possess the miniHPRT and the puΔtk recombination substrate at the same location.

Figure 10:
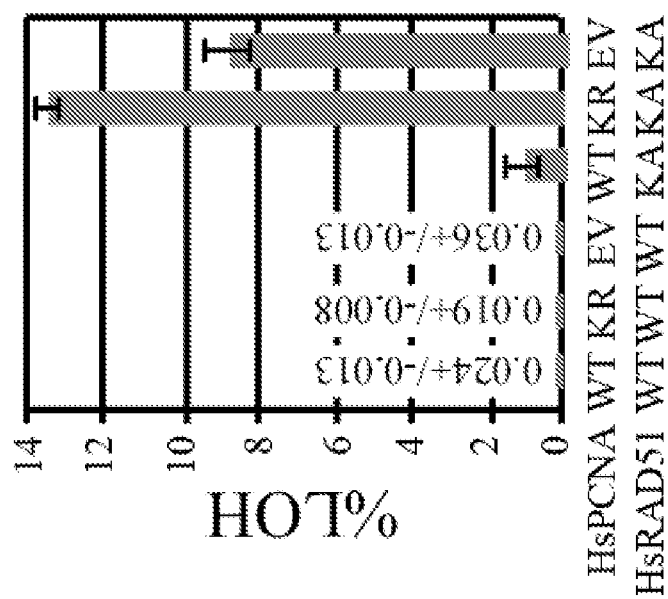
FIG. 10 is a graphical representation of the interaction between PCNA and RAD51, according to an embodiment.

PCNA can conduct both replicative and non-replicative DNA synthesis and is central to controlling DDT as TLS and TS are controlled by mono- and poly-ubiquitinating PCNA K164, respectively. Therefore, 3XFlag-HsPCNA$^{WT}$ or 3XFlag-HsPCNA$^{K164R}$ was expressed in wild type and msh2$^{-/-}$ cells and these cells were compared to those that express empty vector. These vectors were knocked-in adjacent to the TOP3β promoter in WT and msh2$^{-/-}$ cells using Cre-mediated targeting (FIG. 9). This ensures that a clone will express a single transgene from a single location. Cells expressing HsRAD51$^{K133A}$ were generated and expression of 3XFlag-HsPCNA$^{WT}$ reduced loss of heterozygosity as compared to the empty vector control. Expression of 3XFlag-HsPCNA$^{K164R}$ increased loss of heterozygosity as compared to the empty vector control. FIG. 10 is a graphical representation of the interaction between PCNA and RAD51 by expressing 3XFlag-HsPCNA in HsRAD51$^{K133A}$ expressing cells. Compared to cells that express empty vector (EV), expression of 3XFlag-PCNA$^{WT}$ ameliorates loss of heterozygosity while expression of 3XFlag-PCNA$^{K164R}$ exacerbates loss of heterozygosity.

Example 10

A dose response curve can be generated for multiple genotoxins as demonstrated in FIGS. 5A and 5B. The cytotoxicity of the DDT-altered cells to these genotoxins can be evaluated to assess the consequences of applying TX2Is for cancer therapy. As shown in FIGS. 5A and 5B, TREX2-deletion increased cell death when CPT was applied to HsRAD51$^{K133A}$ cells, while HU increased cell death to msh2$^{-/-}$ cells. TREX2-deletion did not increase cell death when applied to otherwise wild type cells for either agent. Thus, TREX2 deletion displayed a synthetic phenotype in RAD51$^{K133A}$ cells and in msh2$^{-/-}$ cells to CPT and HU, respectively.

TX2Is can be evaluated for their effects on cells treated with genotoxins that interact with RFs and agents that do not interact can be evaluated. For example, RF-interacting agents include ultra violet light (UV), hydroxyurea (HU), camptothecin (CPT) and mitomycin C (MMC), while ionizing radiation (IR) is an example of an agent that does not interact with RFs. UV causes helix distorting lesions that stall RFs. HU, CPT, MMC and IR are anti-cancer agents. HU inhibits ribonucleotide reductase to stall RFs. CPT is a type 1 topoisomerase (topo 1) inhibitor that stabilizes a ternary complex between topo 1 and double-stranded DNA resulting in single strand breaks that become DSBs at RFs. CPT also depletes topo 1 to increase positive supercoils ahead of the replication fork. Excessive positive supercoils causes fork regression (a chicken foot). MMC is a bifunctional alkylating agent that forms monoadducts, intra- and interstrand cros slinks. DSBs are formed when the replication fork collides with an interstrand crosslink. Ionizing radiation (IR) directly causes DSBs in DNA that are independent of replication. Flow cytometry can be used to evaluate the cell cycle effects of TX2Is on genotoxin-exposed cells. This evaluation will identify checkpoints and cells in sub-G$_1$ (cell death). A basic cell cycle analysis with BrdU can be used to measure the percentage of cells that enter S phase and with annexin V to measure the number of cells that enter cell death.

These dose response curves can be utilized to provide an effective high dose and low dose for the remaining assays. The two doses for each drug can be chosen based on the survival fraction, such as a high dose being the dose that results in about a 10% survival fraction and a low dose being the dose that results in about a 90% survival fraction. All cells, control and mutants, will be exposed to these doses. If the mutants are hypersensitive or resistant to the agent, then additional doses can be selected to complement those for the control. For the remainder of the experiments described below, a survival fraction will be taken to ensure that the experiments are conducted within these doses.

Example 11

Figure 11:
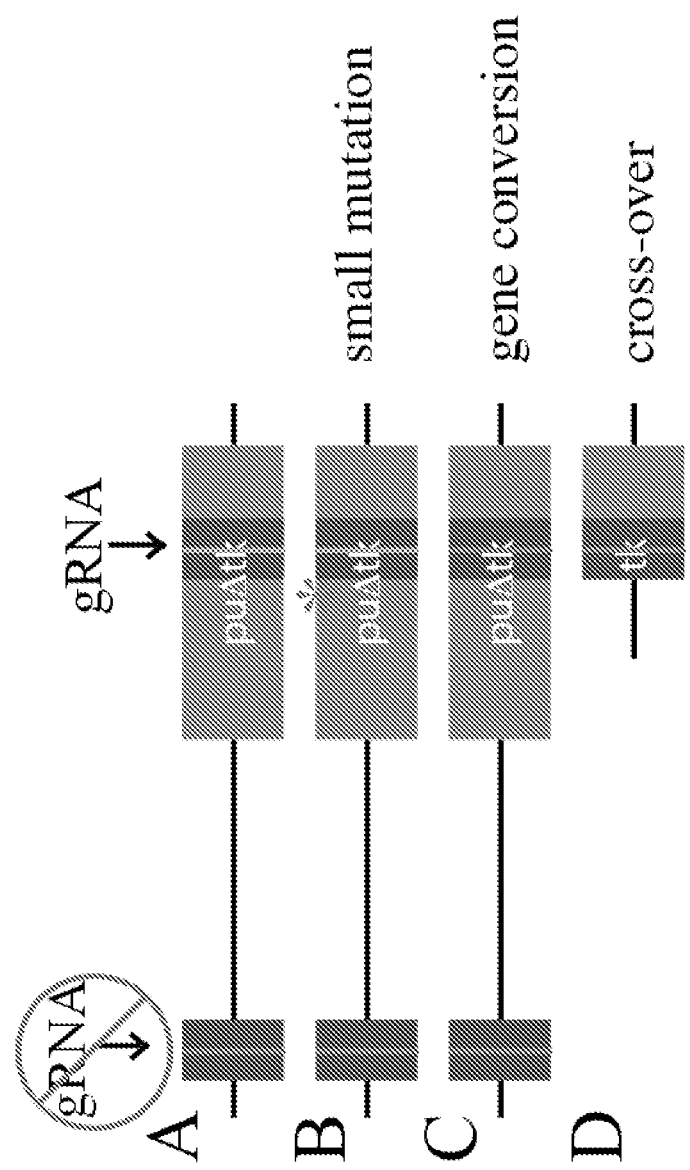
FIG. 11 is a diagrammatic representation of the puΔtk recombination substrate and how the cassette is affected by various chromosomal changes.

Several assays were developed to measure mutations. One such new assay using puzltk recombination substrate was developed to test DNA DSB repair. The puΔtk recombination substrate-based as disclosed here involves a puΔtk sequence that is a positive/negative selection cassette that fuses puromycin N-acetyltransferase (pu) to a truncated version of herpes simplex virus type 1 thymidine kinase (Δtk) generating resistance to puromycin and sensitivity to FIAU [1-(-2-deoxy-2-fluoro-1-β-D-arabino-furanosyl)-5- iodouracil]. Therefore, puΔtk can be used like miniHPRT. FIG. 11 is a diagrammatic representation of the puΔtk recombination substrate and how the cassette is affected by various chromosomal changes. CRISPR-Cas9 with gRNA was used to generate a DSB in puΔtk cassette (shown as a green line in FIG. 11), but a 404 bp substrate, located 1.8 kb away and in a direct orientation, does not have this sequence (shown as a red line in FIG. 11). FIG. 11A presents a puΔtk cassette with a 404 bp substrate. The site of action for the CRISPR-Cas9 and gRNA complex is shown as a green line. The 404 bp substrate is deleted for this sequence, as shown by red line. This is a competition assay as the cells are being selected for loss of function. Therefore, even point mutants (FIG. 11B), gene conversions (FIG. 11C) and cross-overs (FIG. 11D) can be detected using PCR primers and sequencing. Knockin adjacent to the TOP3β promoter generates a miniHPRT and contains a puromycin N-acetyltransferase delta 1 thymidine kinase (puΔtk) recombination substrate that was used to screen for mutations. The miniHPRT as described previously was used by selecting cells in 6-TG. FIG. 11B presents the puΔtk cassette with a small mutation shown as a red asterisk. FIG. 11C presents a puΔtk cassette where the site of action for the CRISPR-Cas9 and gRNA complex is affected due to gene conversion. FIG. 11D presents a puΔtk cassette where the site of action for the CRISPR-Cas9 and gRNA complex and the puromycin N-acetyltransferase portions of the cassette are excised due to a cross-over. Cells will be grown with and without genotoxins and then seeded onto 4 plates: no selection, 6-TG, FIAU, and 6-TG+FIAU. The double selection media will indicate the number of colonies that make a deletion when compared to a plate with either 6-TG or FIAU. This strategy is being deployed in HsRAD51$^{K133A}$ cells and they exhibit >95% of colonies that are resistant to both selections as verified by PCR.

MMR corrects polymerase slippage and regulates recombination in homologous regions (mismatched heteroduplexes) and failure to do either results in gross chromosomal rearrangements. Therefore, two-color fluorescence in situ hybridization (FISH) and spectral karyotyping (SKY) can be employed to analyze chromosomes. The control and mutant cells will be analyzed with and without exposure to a genotoxin as described above. Two-color FISH uses two fluorescent agents to probe the pericentromere in red and the telomere in green. The chromosome is counterstained with DAPI. Using two-color FISH chromatid breaks, isochromatid breaks, and rearranged chromosomes can be visualized and measured. A single broken chromatid is consistent with a broken replication fork. An isochromatid break (break in two complementary sister chromatids at the same location) is consistent with a failed sister chromatid exchange intermediate. Chromosomal rearrangements include dicentrics, EPTs (extra pericentromeres and telomeres), and radials. A dicentric can be caused by the fusion of two chromosomes with deleted telomeres or by defective replication. An EPT is caused by defective replication. A radial is the product of multiple chromosome attachments and is consistent with the fusion of broken chromatids. Each chromosome can be analyzed and a variety of rearrangements can be measured, including the ones visualized by two-color FISH and others like chromosome fusions, deletions and translocations.

Example 12

Figure 12:
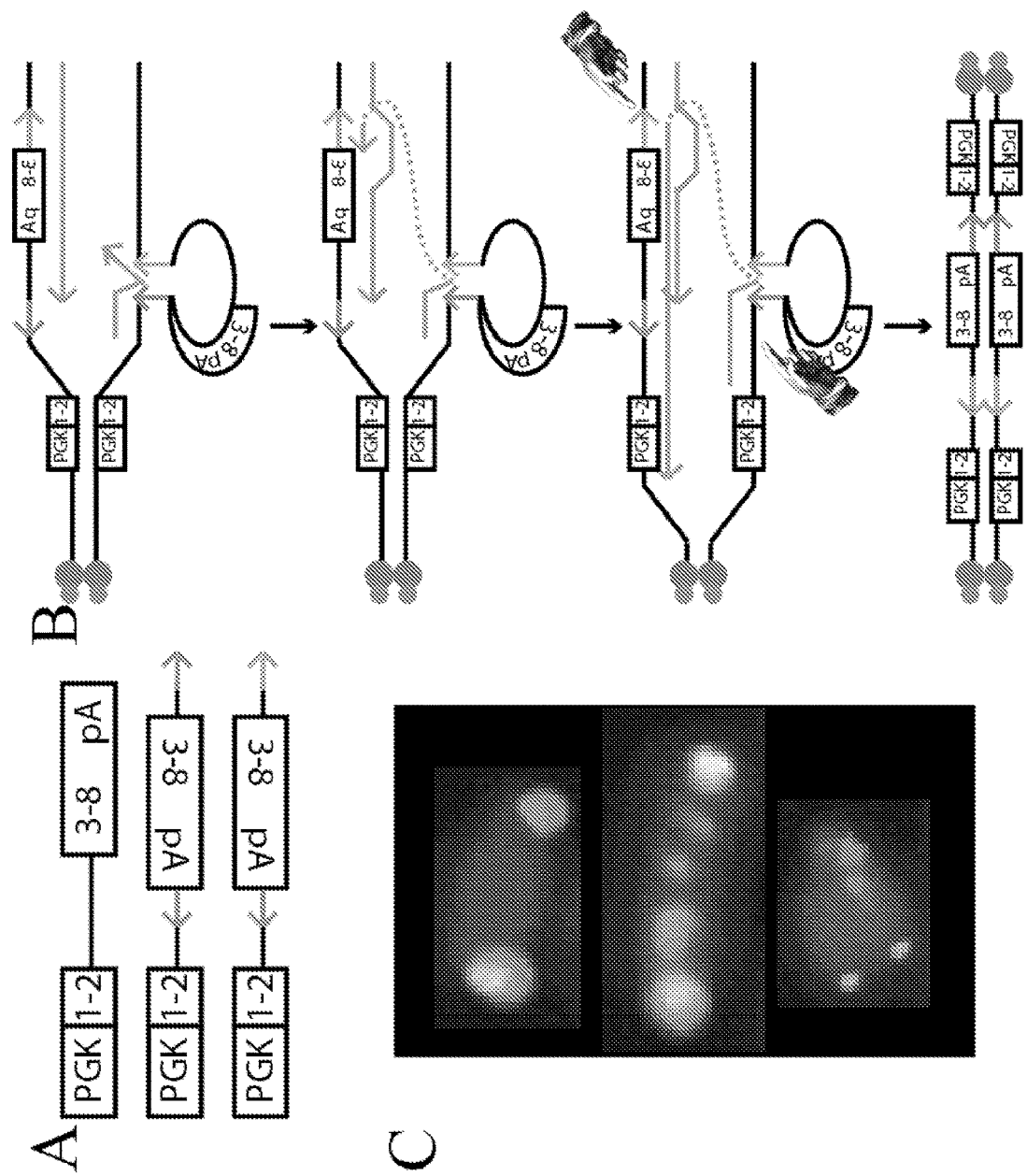
FIG. 12A is a diagrammatic representation of the constructs used in a repeat fusion assay, using an identical repeat reporter (IRR) and a mismatched repeat reporter (MRR), according to an embodiment.
FIG. 12B is a diagrammatic representation of a nonallelic fusion at a stalled replication fork that is then processed to form a dicentric chromosomal arrangement, according to an embodiment.
FIG. 12C is a photographic image of a two-color FISH analysis of metaphase spreads showed chromosomal aberrations for the HAT-resistant colonies, according to an embodiment.

Another new assay involves the measurement of repeat fusion using the identical and mismatched repeat reporters (IRR & MRR) for cells being exposed to the genotoxins as described. The IRR and MRR were designed to investigate pathways that rearrange chromosomes through repeat fusion. Both reporters contain a 313 bp major satellite repeat (MSR) at each junction of an inversion in miniHPRT. FIG. 12A is a diagrammatic representation of the constructs used in a repeat fusion assay, using an identical and a mismatched repeat reporter (IRR & MRR). The top construct in FIG. 12A presents the control miniHPRT construct. The middle construct in FIG. 12A presents the identical repeat construct, and the bottom construct in FIG. 12A presents the mismatched repeat construct. The only difference between these reporters is the MRR's 3' repeat contains seven mismatches with the longest contiguous homology being 67 bps. A 319 bp repeat flanks the location of the inverted exons 3-8. These repeats are indirect, so repeat fusion restores miniHPRT to enable survival in HAT selection media by a potential mechanism shown in FIG. 12B.

FIG. 12B is a diagrammatic representation of a nonallelic fusion at a stalled replication fork. The inverted repeats form a hairpin to stall progression. The nascent strand then attaches to the wrong arrow on the parental strand to cause a dicentric. The fingers point to the locations where nicks must occur to see the dicentric. To measure repeat fusion, miniHPRT will be deleted with flippase as FRTs flank the plasmid backbone, miniHPRT and the puΔtk recombinase substrate (FIG. 9D, blue arrows). Stably transfected IRR and MRR into wild type ES cells resulted in about the same number of spontaneous HAT-resistant colonies. HR-proficient cells (deleted for BLM) exhibited enhanced levels of HAT-resistant colonies with the IRR, but not the MRR. Deletion of a single copy of RAD51 or BRCA2 reversed this increase. On the other hand, deletion of RAD18 or TREX2 caused a decline in HAT-resistant colonies with the MRR, but not the IRR. These results are consistent with homologous recombination controlling repeat fusion with identical repeats and DDT controlling repeat fusion with mismatched repeats. Based on the diagram shown in FIG. 12B, a dicentric or palindromic chromosome will result. Two-color FISH on metaphase spreads showed dicentric chromosomes for the HAT-resistant colonies (FIG. 12C, top). Other types of chromosome aberrations were also found like EPTs (FIG. 12C, middle) and segmental duplications (FIG. 12C, bottom) consistent with the possibility of break-fusion-bridge cycles.

Example 13

Assays were developed to assess the proteins associated with RFs to determine the state of the RFs. These assays can be subsequently employed to evaluate the effects of TREX2 inhibitors on the association of the proteins with RFs. The proteins that are located next to the nascent replication strand were characterized by isolation of proteins on nascent DNA (iPOND) of cells exposed to the genotoxins. This technique isolates proteins at active and damaged RFs at high resolution by labeling the nascent strand with 5-ethynyl-2'-deoxyuridine (EdU) that has an alkyne group and can be covalently linked to a biotin-azide using click chemistry to purify the EdU-labeled strand. These proteins include pRPA32, γ-H2AX, MRE11, RAD51, and histone H3. pRPA32 associates with single strand DNA at replication forks and provides insight about the severity of the response to genotoxins. ATR phosphorylates RPA32 at serine 33 for a mild response. while DNA-PK$_{CS}$ phosphorylates RPA32 at serines 4 and 8 for a severe response. For ES cells, a low HU dose (0.5 mM, 1.5 hours) induced an ATR response, while a high HU dose (4 mM, 5 hours) induced both an ATR and a DNA-PK$_{CS}$ response. High HU dose produced more chromatid breaks indicating collapsed forks with DSBs consistent with the possibility that it signals collapsed forks. A subtype of histone H2A, γ-H2AX is a marker of gaps and DSB breaks. MRE11 is a nuclease that generates the 3' end at a DSB for RAD51 loading. Histone H3 is a loading control.

Figure 13:
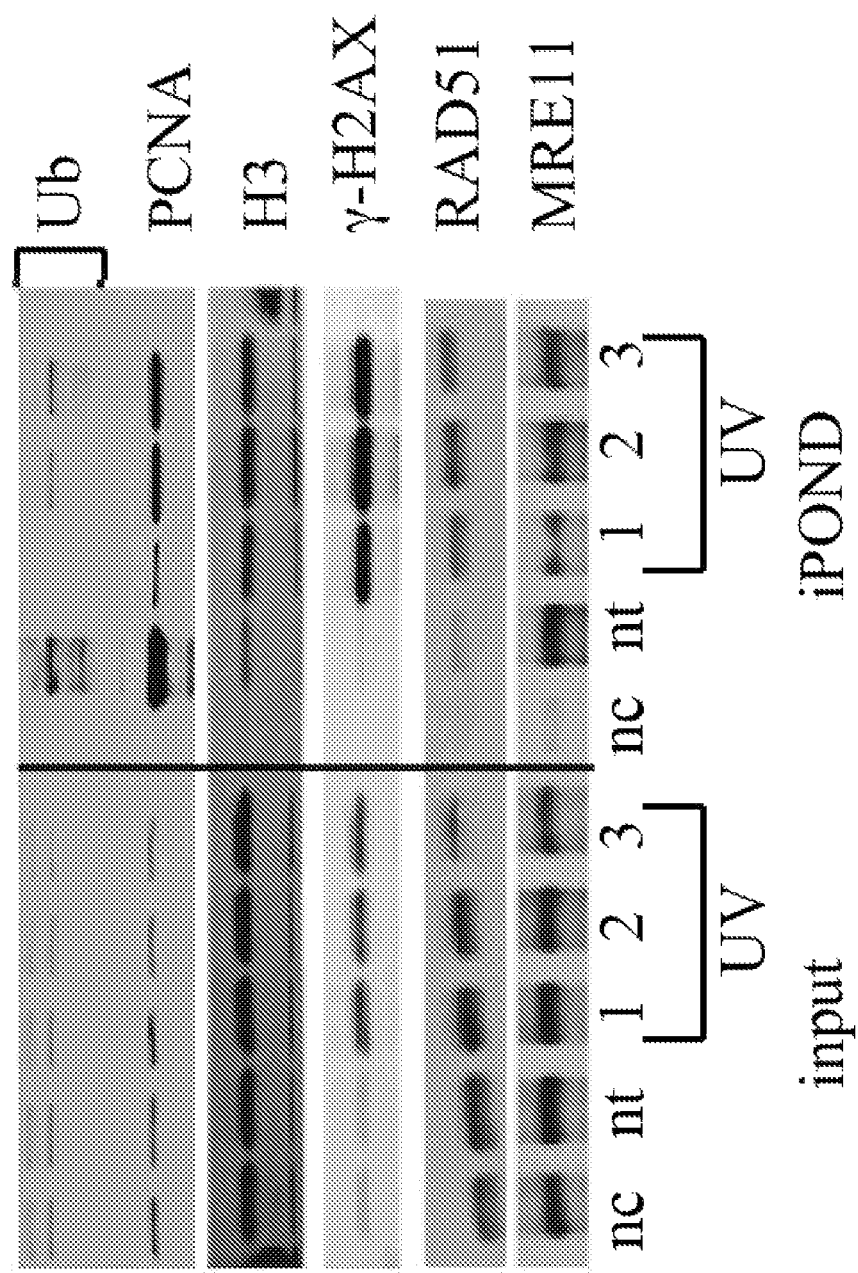
FIG. 13 is a photographic image of an electrophoresis gel-based analysis of proteins from an iPOND assay after exposure of cells to ultraviolet (UV) light, according to an embodiment.

FIG. 13 is a photographic image of an electrophoresis gel-based analysis of proteins from an iPOND assay after exposure of cells to UV. PCNA ubiquitination was also observed using iPOND (FIG. 13, Ub). iPOND will enhance the ability to observe the kinetics of PCNA ubiquitination in the context of other replication-associated proteins. For example, when cells were exposed to 20 J/m$^2$ of UV light using three conditions: (1) EdU for 10 minutes, UV, and no EdU for 1.5 hr, (2) EdU for 10 minutes, UV, and EdU for 1.5 hours, and (3) no EdU, UV, and EdU for 1.5 hours. The first condition detects proteins separated from active replication, while the second and third conditions detect proteins immediately adjacent to the nascent strand. UV decreased the level of PCNA at the nascent strand (FIG. 13, compare no treatment (iPOND, nt) to UV conditions (iPond, UV lanes 1-3). A similar decrease was seen after HU exposure that could be due to unloading at Okazaki fragments. In addition, ubiquitinated PCNA was only detected with conditions 2 and 3 suggesting regulation at the RF.

Example 14

Assays were developed to measure replication fork stalling, nascent strand stability, and fork progression. These assays can be subsequently employed to evaluate the effects of TREX2 inhibitors on replication fork stalling, nascent strand stability, and fork progression. Fiber/combing analysis for cells exposed to the genotoxins (95% survival fraction) directly measures replication fork restart, replication fork stalling, replication fork progression and nascent strand protection. Combing will allow quantitative measurements of fork velocity, fork asymmetry, inter-origin distances, and global instant fork density.

Knockouts of RAD18 and UBC13 would probably result in the same basic phenotype as TREX2-deletion, except their knockouts might be more extensive as they are involved in other pathways. For example, deletion of RAD18 and TREX2 both prohibit mismatch repeat fusion, PCNA ubiquitination, and replication fork stalls. When it comes to the small mutations (polymerase slippage and point mutations) the results from TREX2- and RAD18-deleted cells should be similar. Yet, RAD18-deletion had a mildly negative impact on identical fusion while TREX2-deletion had a positive impact. This is probably due to their different impact on DSB repair. TREX2 deletion increased homologous recombination and NHEJ, while RAD18-deletion diminished homologous recombination suggesting a different phenotype when it comes to the repair of DSBs. If true, then RAD18-deletion, but not TREX2-deletion, will cause fewer gene conversion/cross-overs observed with puΔtk cut with gRNA and there might be more chromosomal rearrangements. The knockout of SHPRH and HLTF will result in a phenotype that is different to TREX2-deletion, as siRNA knockdown of SHPRH and HLTF increased mutations to MMS and UV, respectively.

Example 15

Deletion of genes that regulate MSH2 protein stability cause drug resistance in human leukemia cells. Bone marrow cells can be isolated from bilateral femurs of 5 control and msh2$^{-/-}$ mice and magnetically labeled with biotinylated antibody cocktail against a series of lineage markers, followed by labeling with Anti-Biotin MicroBeads (Miltenyi). The unlabeled lineage negative stem and progenitor cells are then isolated using MidiMACS™ Separator system (Miltenyi). The BM stem/progenitor cells are cultured in vitro in StemSpan™ SFEM base media supplemented with Flt3/Flk-2 Ligand, SCF, IL-3 and IL-6 (Stemcell technologies). After recovering for two days, HAT is added to medium for 7 days to kill 6-TG-resistant cells. Then, 10$^4$ viable cells are counted and applied to semi-solid MethoCult™ GF M3534 medium with the TX2I on to four plates and vehicle on another four plates. Both bone marrow stem cells and progenitor cells are treated with TX2I or vehicle. Twenty-four hours later, two plates with TX2I and two plates with vehicle are exposed to two gray units of ionizing radiation and allowed to grow for five days. The media is changed every day with fresh TX2I or vehicle. 6-TG is added to half plates and incubated at 37° C. degree. 6-TG is not added to the remaining half so that these plates serve as a seeding control. Colonies are monitored and counted. Exposure to ionizing radiation will increase the number of mutations in the HPRT gene and that the addition of the TX2Is will reduce this increase.

Example 16

An in vivo approach can be tested for the best-performing TX2Is from the ex vivo experiment. TX2Is can be injected intraperitoneally (i.p.) into four control and msh2$^{-/-}$ mice using a dose based on the cell studies as a starting point. About 10 μM as a dose would be used as a starting point. To achieve this same 10 μM concentration of the inhibitor in blood, which will serve as a surrogate measurement to achieve the expected in vivo effect in four mice, about 9 mg/kg can be injected once daily for each mouse. The serum, blood and a variety of organs can be analyzed for drug concentration. The half-life can be determined in a separate experiment with four mice. Each mouse can be given an i.p. dose of 9 mg/kg and 50 μL blood samples can be collected from the tail at 30, 60, 120, and 240 min in 2 mice and at 360, 480, and 600 min in 2 mice after the time of injection of the drug. The half-life of the drug can be determined using the pharmacokinetic analysis with Prism2 software. The concentration of TX2I can be quantified in blood and tissue samples using HPLC with UV detection. Four mice can be injected with TX2I i.p. and another four mice with vehicle similar to the ex vivo experiment described earlier. Twenty-four hours later two mice from each group can be exposed to two gray units of ionizing radiation. The TX2I treatments can continue to keep a serum concentration ~50 ppm. The mice can be sacrificed four days later and the BM cells taken, processed and seeded in 6-TG as described above. Exposure to ionizing radiation will increase the number of mutations in the HPRT gene and that the addition of the TX2Is will reduce this increase in the number of mutations.

Whenever a numerical range is indicated herein, it is meant to include any cited numeral (fractional or integral) within the indicated range. It is understood that the examples and embodiments described herein are for illustrative purposes only and that various equivalents, modifications or changes in light thereof will be suggested to persons skilled in the art and are to be included within the spirit and purview of this application and scope of the appended claims.

What is claimed is:

1. A method of identifying an agent that inhibits exonuclease activity of TREX2, said method comprising:

providing an oligonucleotide-based substrate with a reporter associated with 3' end of the oligonucleotide-based substrate and a complementary quencher associated with 5' end of the oligonucleotide-based substrate;

incubating the oligonucleotide-based substrate in the presence of TREX2 and a compound under reaction conditions for a sufficient period of time; and determining amount of reporter disassociated from the oligonucleotide-based substrate, wherein an increase in the amount of reporter disassociated from the oligonucleotide-based substrate indicates that the compound is an agent that inhibits exonuclease activity of TREX2.

2. The method of claim 1, wherein the oligonucleotide-based substrate is a single stranded deoxyribonucleic acid.

3. The method of claim 1, wherein the oligonucleotide-based substrate is a 20 nucleotide-long single stranded deoxyribonucleic acid.

4. The method of claim 1, wherein the reporter is covalently attached to the base of the second to last nucleotide on the 3' end.

5. The method of claim 1, wherein the reporter is located at 25 nucleotides or less from the complementary quencher.

6. The method of claim 1, wherein the reporter is a fluorophore.

7. The method of claim 1, wherein the reporter is Fluorescein.

8. The method of claim 7, wherein the complementary quencher is 4'-(4-Nitro-phenyldiazo)-2'-methoxy-5'-methoxy-azobenzene-4''-(N-2-oxy ethyl (4,4' dimethoxy trityl))-N-ethyl-2-cyanoethyl-(N,N-diisopropyl)-phosphoramidite.

9. The method of claim 1, wherein the reporter is tetramethylrhodamine (TAMRA).

* * * * *